US011545257B1

(12) United States Patent
Gage, Jr. et al.

(10) Patent No.: US 11,545,257 B1
(45) Date of Patent: Jan. 3, 2023

(54) METHODOLOGIES FOR A HEALTH INSURANCE EXCHANGE PLATFORM

(71) Applicant: Empoweredbenefits, LLC, Charlotte, NC (US)

(72) Inventors: Gaston H. Gage, Jr., Charlotte, NC (US); Stephen Gage, Charlotte, NC (US); Robert Mitchell Ellington, Jr., Huntersville, NC (US); Alan Bray Jones, Rock Hill, SC (US); Bradley Haden, Edgemore, SC (US); Richard Pierce, Charlotte, NC (US)

(73) Assignee: EMPOWEREDBENEFITS, LLC, Charlotte, NC (US)

( * ) Notice: Subject to any disclaimer, the term of this patent is extended or adjusted under 35 U.S.C. 154(b) by 715 days.

(21) Appl. No.: 16/551,968

(22) Filed: Aug. 27, 2019

Related U.S. Application Data

(63) Continuation of application No. 15/290,786, filed on Oct. 11, 2016, now abandoned, which is a
(Continued)

(51) Int. Cl.
*G06Q 30/00* (2012.01)
*G16H 40/20* (2018.01)
(Continued)

(52) U.S. Cl.
CPC ......... *G16H 40/20* (2018.01); *G06Q 10/1053* (2013.01); *G06Q 30/0207* (2013.01); *G06Q 30/0215* (2013.01); *G06Q 30/0603* (2013.01); *G06Q 30/0623* (2013.01); *G06Q 30/0633* (2013.01)

(58) Field of Classification Search
None
See application file for complete search history.

(56) References Cited

U.S. PATENT DOCUMENTS 5,732,401 A 3/1998 Conway
6,092,047 A 7/2000 Hyman et al.
(Continued)

OTHER PUBLICATIONS

Information Disclosure Statement (IDS) Letter Regarding Common Patent Application(s), dated Oct. 31, 2019.
(Continued)

*Primary Examiner* — Mila Airapetian
(74) *Attorney, Agent, or Firm* — Tillman Wright, PLLC; James D. Wright; David R. Higgins

(57) ABSTRACT

A method for facilitating employee selection of one or more health insurance products includes displaying specific defined contribution amounts for health insurance products; receiving, from the user, input corresponding to selection of a health insurance product; displaying, to the user, information regarding the selected insurance product including an estimated cost of a plan including the selected health insurance product, a coupon amount the cost of the plan will be discounted based on a specific defined contribution amount for the class of the selected health insurance product, a lump sum defined contribution amount the cost of the plan will be discounted, and an estimated monthly cost after the coupon amount and lump sum defined contribution amount are applied.

20 Claims, 58 Drawing Sheets

Related U.S. Application Data continuation-in-part of application No. 15/081,626, filed on Mar. 25, 2016, now abandoned.

(60) Provisional application No. 62/137,951, filed on Mar. 25, 2015.

(51) Int. Cl.
*G06Q 30/02* (2012.01)
*G06Q 30/06* (2012.01)
*G06Q 10/10* (2012.01)

(56) References Cited

U.S. PATENT DOCUMENTS

| | | |
|---|---|---|
| 8,489,432 B1 | 7/2013 | Smith |
| 8,670,996 B1 | 3/2014 | Weiss |
| 2002/0128879 A1 | 9/2002 | Spears |
| 2003/0009355 A1 | 1/2003 | Gupta |
| 2004/0039608 A1 | 2/2004 | Mazur et al. |
| 2005/0261939 A1 | 11/2005 | Augspurger et al. |
| 2007/0043595 A1 | 2/2007 | Pederson |
| 2007/0055601 A1 | 3/2007 | Inderski et al. |
| 2009/0094055 A1 | 4/2009 | Gage, Jr. et al. |
| 2010/0094663 A1 | 4/2010 | Spriggs |
| 2011/0022479 A1 | 1/2011 | Henley |
| 2012/0303379 A1 | 11/2012 | Lash |
| 2014/0114674 A1 | 4/2014 | Krughoff et al. |
| 2016/0125362 A1 | 5/2016 | Dziuba et al. |
| 2016/0232628 A1* | 8/2016 | Witala ................. G06Q 50/167 |
| 2016/0239807 A1 | 8/2016 | Creighton et al. |

OTHER PUBLICATIONS

270/271 Healthcare Eligibility Benefit Inquiry and Response Companion Guide, Aug. 3, 2006, Valueoptions, Version 1.1, <http://www.valueoptions.com/providers/Compliance/270_271_Companion_Guide.pdf.

* cited by examiner

FIG. 1

Marketplace | BROKER

Signed in as John Doe | My Groups | Sign Out

All Groups >
ABC Inc.

No Plan Years Currently Set Up

Create Plan Year

Activity Log

Show 10 Most Recent Activities >

Enter activity for this group

Post

Brokers   *Edit*
John Doe - Primary

Contact Information
ABC Inc.

1234 Elm Street
Charlotte, NC 28277
704-248-1234
contact@abc.com

Group Administrators   *Edit*
Company HR
James Miller
james@abc.com

Billing Information   *Edit*
Contact: James Miller
1234 Elm Street
Charlotte, NC 28277
704-248-1234
contact@abc.com
Deducation Frequency: Monthly Deactivate Group

*FIG. 7*

Marketplace | BROKER

Signed in as John Doe | My Groups | Sign Out

All Groups > ABC Inc.
Create Plan Year

| Basic Information | Broker Assignment | Plan Choices | Carrier Forms | Verify & Submit |

Basic Information

Enrollment Dates

Start Date 📅    End Date 📅

Employee Census Input Method
- ◉ Upload Census File    ○ Enter Census Summary Data and Prompt Group Admin to Upload Census File

Upload Census File (download template)

[ Select File to Upload ]  [ Browse ]

Coverage Dates

Start Date 📅    End Date 📅

|  | Total | Male | Female | 15-24 | 25-34 | 35-44 | 45-54 | 55-64 | 65+ |
|---|---|---|---|---|---|---|---|---|---|
|  | n/a | n/a | n/a | n/a | n/a | n/a | n/a | n/a | n/a |

[ Continue ]  [ Cancel ]

*FIG. 8*

Marketplace | BROKER

Signed in as John Doe | My Groups | Sign Out

All Groups > ABC Inc.
Create Plan Year

| Basic Information | Broker Assignment | Plan Choices | Carrier Forms | Verify & Submit |

Basic Information

Enrollment Dates
06/24/2014 📅   06/28/2014 📅

Coverage Dates
07/01/2014 📅   06/30/2015 📅

Employee Census Input Method
◉ Upload Census File    ○ Enter Census Summary Data and Prompt Group Admin to Upload Census File

Upload Census File (download template)
[ ABC_census.xlsx  × ]   [ Upload ]

| Total | Male | Female | 15-24 | 25-34 | 35-44 | 45-54 | 55-64 | 65+ |
|---|---|---|---|---|---|---|---|---|
| n/a | n/a | n/a | n/a | n/a | n/a | n/a | n/a | n/a |

[ Continue ]   [ Cancel ]

Marketplace | BROKER     Signed in as John Doe | My Groups | Sign Out

All Groups > AB...

Create F...

Assign New Broker
Step 1 of 2: Find Broker

| NC – North Carolina ∨ | Show All Products ∨ | Enter Last Name 🔍 |

Joe Russell
Big Insurance Co.
NC License No. 143942 | NPN No. 24443
NC and 1 other state
704-591-3517 | jrussell@big.com Carrier Appointments
Aflac      Humana
Aetna     Allstate
BCBS
VSP

[Select Broker]

Keri Chambers
Sky Insurance Co.
NC License No. 143542 | NPN No. 12456
NC and 2 other states
704-445-6245 | kchambers@sky.com Carrier Appointments
Aflac      Humana
Delta
BCBS
VSP

[Select Broker]

Robert Smith
AB Insurance Co.
NC License No. 445942 | NPN No. 76423
NC and 4 other states
704-694-3414 | rsmith@ab.com Carrier Appointments
Aflac
BCBS
VSP

[Select Broker]

[Cancel]

*FIG. 10B*

Marketplace | BROKER

Signed in as John Doe | My Groups | Sign Out

All Groups > ABC Inc.
Create Plan Year

| Basic Information | Broker Assignment | Plan Choices | Carrier Forms | Commission Split | Verify & Submit |

Broker Assignment
Please review the brokers assigned to this group. To add a co-broker, click the Assign New Broker button.

[+] Assign New Broker

John Doe
XYZ Insurance Co.
NC License No. 392932 | NPN No. 15341
NC and 3 other states
704-892-4526 | jdoe@xyz.com

Carrier Appointments
BCBS    Humana
Allstate    TransAm
VSP    Unum
Delta

✓ Account Owner

Joe Russell
Big Insurance Co.
NC License No. 143942 | NPN No. 24443
NC and 1 other state
704-591-3517 | jrussell@big.com

Carrier Appointments
Aflac    Humana
Aetna    Allstate
BCBS
VSP

Waiting on Confirmation
*Cancel Invitation*

[ Continue ]   [ Cancel ]   [ Go Back ]

◯ Marketplace | BROKER

Signed in as John Doe | My Groups | Sign Out

All Groups > ABC Inc.
Create Plan Year

| Basic Information | Broker Assignment | Plan Choices | Carrier Forms | Verify & Submit |

Broker Assignment
Please review the brokers assigned to this group. To add a co-broker, click the Assign New Broker button.

[+] Assign New Broker

John Doe
XYZ Insurance Co.
NC License No. 392932 | NPN No. 15341
NC and 3 other states
704-892-4526 | jdoe@xyz.com

Carrier Appointments
BCBS    Humana
Allstate    TransAm
VSP    Unum
Delta

↙ Account Owner

Joe Russell
Big Insurance Co.
NC License No. 143942 | NPN No. 24443
NC and 1 other state
704-591-3517 | jrussell@big.com

Carrier Appointments
Aflac    Humana
Aetna    Allstate
BCBS
VSP

Waiting on Confirmation
*Cancel Invitation*

[Continue]  [Cancel]    [Go Back]

You are currently in Face-to-Face Mode. | *Switch to Broker-Only Mode.*

○ Marketplace | BROKER

Signed in as John Doe | My Groups | Sign Out

All Groups > ABC Inc.
Create Plan Year

| Basic Information | Broker Assignment | Plan Choices | Carrier Forms | Verify & Submit |

Verify and Submit to Group Admin

Basic Information | *Edit*
*Complete* 59 Employees | Census Uploaded
2014-2015 Plan Year
Coverage Dates: 2014-07-01 to 2015-06-30
Enrollment Dates: 2014-06-24 to 2014-06-28

Broker Assignment | *Edit*
*Complete* John Doe | Owner

Carrier Forms | *Edit*
*Complete* BCBS: Complete     Allstate: Complete
Delta: Complete     Unum: Complete
VSP: Complete     Humana: Complete
TransAm: Complete

Plan Choices | *Edit*
*Complete*
*Medical*
BCBS: Blue Options Gold
BCBS: Blue Options Silver
*Dental*
Delta Dental: Delta Dental PPO Option A
Delta Dental: DeltaCare USA Copay Plan
*Vision*
VSP Vision Care: Platinum Plan

*Critical Illness*
TransAmerica: Critical Assistance Advance
Allstate Benefits: Group Critical Illness
*Accident*
Unum: Individual Accident Insurance On-Off Job
*Term Life*
Humana: Term Life – 10 Yr.
Humana: Term Life – 20 Yr.

*Whole Life*
TransAmerica: TranSure - Employee
TransAmerica: TranSure – Spouse
TransAmerica: TranSure – 10k Child Term Life Rider
*Universal Life*
Allstate Benefits: Universal Life – High Employee
Allstate Benefits: Universal Life – High Spouse
Allstate Benefits: Universal Life – 10k Child Term Life

[ Submit to Group Admin ]     [ Cancel ]     [ Go Back ]

*FIG. 17*

Marketplace | GROUP

| Overview | Employees ˅ | Products/Plans | Carriers | Administrators | Reporting |

ABC Inc.: 2014-2015 Plan Year
Signed in as James Miller | My Groups | Sign Out

Group Overview

Group Number: 1415ABC

ABC Inc. | *Edit*
1234 Elm Street
Charlotte, NC 28277
704-248-1234
contact@abc.com

Current Plan Year
2014-2015 Plan Year
Coverage Start Date: 07/01/2014
Coverage End Date: 06/30/2015

Open Enrollment Dates
06/24/2014 – 06/28/2014

Broker(s)
John Doe
XYZ Insurance Co.
704-892-4526
jdoe@xyz.com

Census Summary

| Total | Male | Female | 15-24 | 25-34 | 35-44 | 45-54 | 55-64 | 65+ |
|---|---|---|---|---|---|---|---|---|
| 59 | 55 | 4 | 44 | 4 | 1 | 10 | 0 | 0 |

Carriers
Humana    Delta          VSP
Allstate   TransAmerica
Unum       BCBS

FIG. 19

Marketplace | GROUP

ABC Inc.: 2014-2015 Plan Year
Signed in as James Miller | My Groups | Sign Out

| Overview | Employees ⌄ | Products/Plans | Carriers | Administrators | Reporting |

All Employees: Search

[Add New Employee]  [Upload New Census]

[Show Active ⌄]  [🔍 Search for an Employee]

| Name | SSN | Gender | Email | Status |
|---|---|---|---|---|
| Bill Bradley | xxx-xx-4789 | Male | bbradley@abc.com | Not Registered |
| John Brazid | xxx-xx-2179 | Male | jbrazid@abc.com | Not Registered |
| Ron Christmas | xxx-xx-8219 | Male | rchristmas@abc.com | Not Registered |
| Janet Cili | xxx-xx-1144 | Female | jcili@abc.com | Not Registered |
| Ron Dill | xxx-xx-6781 | Male | rdill@abc.com | Not Registered |
| Jim Down | xxx-xx-1546 | Male | jdown@abc.com | Not Registered |

Marketplace | GROUP

ABC Inc.: 2014-2015 Plan Year
Signed in as James Miller | My Groups | Sign Out

| Overview | Employees ˅ | Products/Plans | Carriers | Administrators | Reporting |

Sign In as Employer    Terminate

All Employees >
Bill Bradley

- Employee Information
- Dependents
- Qualifying Events
- *Coverage Summary*
- Comments Log

Coverage Summary: Eligible Products

Defined Contribution Amount [          ]   Save

Medical: Not Enrolled
Eligible for coverage | *Add*          Total Cost          Contribution          Employee Cost

Dental: Not Enrolled
Eligible for coverage | *Add*          Total Cost          Contribution          Employee Cost

Vision: Not Enrolled
Eligible for coverage | *Add*          Total Cost          Contribution          Employee Cost

Critical Illness: Not Enrolled
Eligible for coverage | *Add*          Total Cost          Contribution          Employee Cost

Accident: Not Enrolled
Eligible for coverage | *Add*          Total Cost          Contribution          Employee Cost

Term Life: Not Enrolled
Eligible for coverage | *Add*          Total Cost          Contribution          Employee Cost

*FIG. 32*

Marketplace | GROUP

ABC Inc.: 2014-2015 Plan Year
Signed in as James Miller | My Groups | Sign Out

| Overview | Employees∨ | Products/Plans | Carriers | Administrators | Reporting |

All Employees: Defined Contribution

Apply Global Contribution for All Employees

Additional Amount    Total Amount
$ [ 500.00 ]    or    $ [        ]    [ Apply ]

Contribution Per Employee

| Employee Name | Annual Salary | Minimum Contribution | Additional Contribution | Total Defined Contrib. Amount |
|---|---|---|---|---|
| Bill Bradley | $46,500 | $3,500.00 | $500.00 | $ 4000.00 |
| John Brazid | $54,500 | $3,500.00 | $500.00 | $ 4000.00 |
| Ron Christmas | $96,400 | $3,500.00 | $500.00 | $ 4000.00 |
| Janet Cili | $78,200 | $3,500.00 | $500.00 | $ 4000.00 |
| Ron Dill | $24,000 | Contribution does not meet ACA standards. | | $ 2750.00 |

[ Save Changes ]  [ Reset ]

*FIG. 33*

Marketplace | GROUP

ABC Inc.: 2014-2015 Plan Year
Signed in as James Miller | My Groups | Sign Out

| Overview | Employees ˅ | Products/Plans | Carriers | Administrators | Reporting |

Products/Plans

| Product | Carrier | Plan | Plan Details | Availability Dates |
|---|---|---|---|---|
| Medical | BCBS | Blue Options Gold | Brochure | 07/01/2014, ongoing |
| | BCBS | Blue Options Silver | Brochure | 07/01/2014, ongoing |
| Dental | Delta | Delta Dental PPO Option A | Brochure | 07/01/2014, ongoing |
| | Delta | DeltaCare USA Copay Plan | Brochure | Video | 07/01/2014, ongoing |
| Vision | VSP | Platinum Plan | Brochure | 07/01/2014, ongoing |
| Critical Illness | TransAm | Critical Assistance Advance | Brochure | 07/01/2014, ongoing |
| | Allstate | Group Critical Illness | Brochure | 07/01/2014, ongoing |
| Accident | Unum | Individual Accident Insurance On-Off Job | Brochure | 07/01/2014, ongoing |

*FIG. 34*

| | | | | ABC Inc.:: 2014-2015 Plan Year |
| | | | | Signed in as James Miller \| My Groups \| Sign Out |

Marketplace \| GROUP

| Overview | Employees ⌄ | Products/Plans | Carriers | Administrators | Reporting |

Administrators

[ Create New Administrator ]

| Administrator Name | Message | Role Name | Action |
|---|---|---|---|
| James Miller | | COMPANY HR | *Edit \| Remove* |

*FIG. 36*

Marketplace | GROUP

ABC Inc.: 2014-2015 Plan Year
Signed in as James Miller | My Groups | Sign Out

| Overview | Employees ∨ | Products/Plans | Carriers | Administrators | Reporting |

Reporting

Payroll Report
A report designed to help you manage employee payroll deductions and defined contributions.
[Download Report]

Demographic Report
A report to be used for updating your employee records. Contains census data for active and terminated employees and their dependents.
[Download Report]

Enrollment Report
A report of all group enrollments your employees have obtained through this Marketplace.
[Download Report]

*FIG. 37*

○ Marketplace | Employee                                    Signed in as Bill Bradley | Sign Out

| Home | Benefits | Wellness | Resources | My Elections | Messages |

Shop for Benefits

You have made 7 elections totaling $194.73.                    You Pay: $194.73 per month

| | | |
|---|---|---|
| Medical – BCBS Options Gold | $113.40 | |
| Dental | – | |
| Vision – VSP Platinum | $7.06 | |
| Critical Illness – Declined | $0.00 | |
| Accident – Declined | $0.00 | |
| Term Life – Humana 10 YR | $52.40 | |
| Whole Life – Declined | $0.00 | |
| Universal Life – Allstate Univ. | $21.87 | |
| Total Cost of Elections | $194.73 | |

Medical
BCBS
Blue Options Gold
$113.40 / month
*Edit My Election*

Dental
[ View Plans ]

Vision
VSP
Platinum Plan
$7.06 / month
*Edit My Election*

Critical Illness
Declined ✗
*Edit My Election*

Accident
Declined ✗
*Edit My Election*

Term Life
Humana
10 Year Term Life
$52.40 / month
*Edit My Election*

Whole Life
Declined ✗
*Edit My Election*

Univ. Life
Allstate
Universal Life
$21.87 / month
*Edit My Election*

[ Proceed to Benefit Summary ]

*FIG. 40*

○ Marketplace | Employee

Signed in as Bill Bradley | Sign Out

| Home | Benefits | Wellness | Resources | My Elections | Messages |

Shop for Benefits

You have made 7 elections totaling $194.73.    Contribution Amount: $150.00    You Pay: $44.73 per month

| | | | |
|---|---|---|---|
| Medical – BCBS Options Gold | $113.40 | Medical<br>BCBS<br>Blue Options Gold<br>$113.40 / month<br>*Edit My Election* | Dental<br><br>View Plans | Vision<br>VSP<br>Platinum Plan<br>$7.06 / month<br>*Edit My Election* | Critical Illness<br>Declined<br>✗<br>*Edit My Election* |
| Dental | – |
| Vision – VSP Platinum | $7.06 |
| Critical Illness – Declined | $0.00 |
| Accident – Declined | $0.00 | Accident<br>Declined<br>✗<br>*Edit My Election* | Term Life<br>Humana<br>10 Year Term Life<br>$52.40 / month<br>*Edit My Election* | Whole Life<br>Declined<br>✗<br>*Edit My Election* | Univ. Life<br>Allstate<br>Universal Life<br>$21.87 / month<br>*Edit My Election* |
| Term Life – Humana 10 YR | $52.40 |
| Whole Life – Declined | $0.00 |
| Universal Life – Allstate Univ. | $21.87 |

Contribution Applied         $150.00

Total Cost of Elections      $44.73

Proceed to Benefit Summary

*FIG. 41*

2015 Plan Year
Employer Discount Coupons

| Benefit Products | Employee Only | Employee and Spouse | Employee and Children | Employee and Family |
|---|---|---|---|---|
| Medical<br>Offered by: BCBS | $100 discount | $200 discount | $200 discount | $300 discount |
| Dental<br>Offered by: Delta | $100 discount | $200 discount | $200 discount | $300 discount |
| Critical Illness<br>Offered by: Allstate | $100 discount | $200 discount | $200 discount | $300 discount |
| Accident<br>Offered by: Unum | $100 discount | $200 discount | $200 discount | $300 discount |
| Whole Life<br>Offered by: TransAmerica | $100 discount | $200 discount | $200 discount | $300 discount |

[ Return to Homepage ]  [ Start Shopping ]

*FIG. 42*

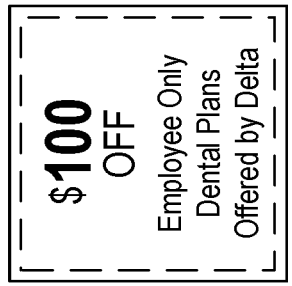
FIG. 43

Marketplace | Employee

Signed in as Mike Zimmer | Sign Out

| Home | Benefits | Wellness | Resources | My Elections | Messages |

Shop for Benefits

*Medical*
Dental
Vision
Critical Illness
Accident
Term Life
Whole Life
Universal Life

Medical Plans

Viewing 6 of 14 plans starting at $540.00 / mo.
Based on your profile below, we are showing only the plans that are the best fit. | *Show all plans*

[ Male, 46 ⌄ ] [ Married ⌄ ] [ Children info ⌄ ] [ Network Prefs ⌄ ] [ Usage Prefs ⌄ ] [ Conditions ⌄ ]

[ Compare Plans ]        [ Compare ]       Sort Plans: [ Price ⌄ ]

☐
United Healthcare
UHC Bronze
Employee and Family

| Deductible | $4000 |
| Coinsurance | 0% |
| Visit (Primary) | $50 |
| Visit (Spec.) | $100 |
| Dr. Smith Covered? | Yes |
| Dr. Weinstein Covered? | No |

$641.78 / mo.
(after $300 employer coupon)

[ Plan Details ]  [ Add to Cart ]

☐
United Healthcare
UHC Silver
Employee and Family

| Deductible | $3000 |
| Coinsurance | 0% |
| Visit (Primary) | $50 |
| Visit (Spec.) | $100 |
| Dr. Smith Covered? | Yes |
| Dr. Weinstein Covered? | No |

$760.38 / mo.
(after $300 employer coupon)

[ Plan Details ]  [ Add to Cart ]

☐
United Healthcare
UHC Gold
Employee and Family

| Deductible | $1000 |
| Coinsurance | 0% |
| Visit (Primary) | $50 |
| Visit (Spec.) | $100 |
| Dr. Smith Covered? | Yes |
| Dr. Weinstein Covered? | No |

$793.54 / mo.
(after $300 employer coupon)

[ Plan Details ]  [ Add to Cart ]

Marketplace | Employee

Signed in as Mike Zimmer | Sign Out

| Home | Benefits | Wellness | Resources | My Elections | Messages |

Shop for Benefits

*Medical*
Dental
Vision
Critical Illness
Accident
Term Life
Whole Life
Universal Life

Medical Plans

Viewing 6 of 14 plans starting at $540.00 / mo.
Based on your profile below, we are showing only the plans that are the best fit. | *Show all plans*

[ Male, 46 ∨ ] [ Married ∨ ] [ Children info ∨ ] [ Network Prefs ∨ ] [ Usage Prefs ∨ ] [ Conditions ∨ ]

[ Compare Plans ]  [ UHC Bronze ☒ ]  [ UHC Silver ☒ ]  [ Compare ]  Sort Plans: [ Price ∨ ]

---

United Healthcare
UHC Bronze
Employee and Family ☒

| | |
|---|---|
| Deductible | $4000 |
| Coinsurance | 0% |
| Visit (Primary) | $50 |
| Visit (Spec.) | $100 |
| Dr. Smith Covered? | Yes |
| Dr. Weinstein Covered? | No |

$641.78 / mo.
(after $300 employer coupon)

[ Plan Details ]  [ Add to Cart ]

---

United Healthcare
UHC Silver
Employee and Family ☒

| | |
|---|---|
| Deductible | $3000 |
| Coinsurance | 0% |
| Visit (Primary) | $50 |
| Visit (Spec.) | $100 |
| Dr. Smith Covered? | Yes |
| Dr. Weinstein Covered? | No |

$760.38 / mo.
(after $300 employer coupon)

[ Plan Details ]  [ Add to Cart ]

---

United Healthcare
UHC Gold
Employee and Family ☐

| | |
|---|---|
| Deductible | $1000 |
| Coinsurance | 0% |
| Visit (Primary) | $50 |
| Visit (Spec.) | $100 |
| Dr. Smith Covered? | Yes |
| Dr. Weinstein Covered? | No |

$793.54 / mo.
(after $300 employer coupon)

[ Plan Details ]  [ Add to Cart ]

*FIG. 46*

Marketplace | Employee

Signed in as Bill Wall | Sign Out

| Home | Benefits | Wellness | Resources | My Elections | Messages |

Shop for Benefits

Medical Plans

*Medical*

*Dental*

*Vision*

*Accident*

*Critical Illness*

*Term Life*

United Healthcare
UHC Bronze
Employee and Family

| Deductible | $4000 |
| Coinsurance | 0% |
| Visit (Primary) | $50 |
| Visit (Spec.) | $100 |
| Dr. Smith Covered? | Yes |
| Dr. Weinstein Covered? | No |

$641.78 / mo.
(after $300 employer coupon)

[Plan Details]  [Add to Cart]

United Healthcare
UHC Silver
Employee and Family

| Deductible | $3000 |
| Coinsurance | 0% |
| Visit (Primary) | $50 |
| Visit (Spec.) | $100 |
| Dr. Smith Covered? | Yes |
| Dr. Weinstein Covered? | No |

$760.38 / mo.
(after $300 employer coupon)

[Plan Details]  [Add to Cart]

United Healthcare
UHC Gold
Employee and Family

| Deductible | $1000 |
| Coinsurance | 0% |
| Visit (Primary) | $50 |
| Visit (Spec.) | $100 |
| Dr. Smith Covered? | Yes |
| Dr. Weinstein Covered? | No |

$793.54 / mo.
(after $300 employer coupon)

[Plan Details]  [Add to Cart]

Your enrollment progress so far...
Plan choices made: 4
Required choices remaining: 2
Estimated Plan Cost: $829.76 / mo.
Estimated Coupons: - $300.00 / mo.
Benefit Bank: - $214.00 / mo.
My Total Estimated Cost: $315.76 / mo.

My Benefit Score
83 out of 100
Very Good
Enroll in Dental and Vision coverage for optimal coverage.

Marketplace | Employee                                          Signed in as Bill Wall | Sign Out

| Home | Benefits | Wellness | Resources | My Elections | Messages |

2014 Open Enrollment: My Elections

| Product | Plan Name | Est. Plan Cost | Est. Coupons | My Est. Cost | Actions |
|---|---|---|---|---|---|
| Medical | BCBS Gold | $651.26 / mo. | $250.00 / mo. | $401.26 / mo. | Edit | Decline |
| Dental | | | | | Shop Plans | Decline |
| Vision | | | | | Shop Plans | Decline |
| Accident | Unum On-Off Job | $95.43 / mo. | $50.00 / mo. | $45.43 / mo. | Edit | Decline |
| Critical Illness | Allstate CI | $45.24 / mo. | | $45.24 / mo. | Edit | Decline |
| Term Life | Allstate Short Term Disability | $37.83 / mo. | | $37.83 / mo. | Edit | Decline |
| Estimated Total | Estimated Total for All Plans | $829.76 / mo. | $300.00 / mo. | $519.76 / mo. | |
| | Benefit Bank: | | | $214.00 / mo. | |
| | My Total Estimated Cost for Elections: | | | $315.76 / mo. | Checkout |

FIG. 48

Marketplace | Employee

Signed in as Bill Wall | Sign Out

| Home | Benefits | Wellness | Resources | My Elections | Messages |

My Elections
Checkout

Save Checkout Progress

Total Cost of Elections (Includes $x of Employer Contribution): [ 2% ] $519.76

---

Medical (BCBS Gold)
*Confirm Coverage Tier*

1. Medical
 - *Confirm Coverage Tier*
 - HSA Election
 - Review / Confirm Coverage Select the coverage tier that best suits the needs of your family:

○ Employee Only
○ Employee and Spouse
○ Employee and Children
● Employee and Family

2. Dental

3. Vision

4. Accident

The Employee and Family Tier will cover the following people:   *Add/Edit Dependents*

1. Bill Wall (Employee)
2. Diana Wall (Spouse)
3. Hunter Wall (Child – Age 11)

5. Critical Illness

6. Term Life

7. Confirm Enrollment

[ Continue to Next Step ]   [ Go Back ]

📝 Edit Elections

*FIG. 49*

Marketplace | Employee

Signed in as Mike Zimmer | Sign Out

| Home | Benefits | Wellness | Resources | My Elections | Messages |

Shop for Benefits

Bundles

- Medical
- Dental
- Vision
- Critical Illness
- Accident
- Term Life
- Whole Life
- Universal Life
- *Bundles*

Viewing 6 of 13 bundles starting at $742.00 / mo.
Based on your profile below, we are showing only the plans that are the best fit. | *Show all plans*

[Male, 46 ⌄] [Married ⌄] [Children info ⌄] [Network Prefs ⌄] [Usage Prefs ⌄] [Conditions ⌄]

Compare Plans    [Compare]    Sort Plans: [Price ⌄]

---

Young Family
Bronze Coverage  ☐

| UHC Bronze | $641.78 |
| VSP Vision Platinum | $7.06 |
| Delta Dental | $57.23 |

$706.07 / mo.
(after $300 employer coupon)

[View Details] [Add to Cart]

---

Young Family
Silver Coverage  ☐

| UHC Silver | $760.38 |
| VSP Vision Platinum | $7.06 |
| Delta Dental | $57.23 |

$824.67 / mo.
(after $300 employer coupon)

[View Details] [Add to Cart]

---

Young Family
Gold Coverage  ☐

| UHC Gold | $793.54 |
| VSP Vision Platinum | $7.06 |
| Delta Dental | $57.23 |

$857.83 / mo.
(after $300 employer coupon)

[View Details] [Add to Cart]

*FIG. 50*

METHODOLOGIES FOR A HEALTH INSURANCE EXCHANGE PLATFORM

CROSS-REFERENCE TO RELATED APPLICATION

The present application is a U.S. continuation patent application of, and claims priority under 35 U.S.C. § 120 to, U.S. non-provisional patent application Ser. No. 15/290,786, filed Oct. 11, 2016, which '786 application is a U.S. continuation-in-part patent application of, and claims priority under 35 U.S.C. § 120 to, U.S. non-provisional patent application Ser. No. 15/081,626, filed Mar. 25, 2016, which '626 application is a U.S. non-provisional patent application of, and claims priority under 35 U.S.C § 119(e) to, U.S. provisional patent application Ser. No. 62/137,951, filed Mar. 25, 2015. Each of the foregoing patent applications is expressly incorporated by reference herein.

The present application hereby incorporates herein by reference the disclosure of Exhibits 1 and 2 attached hereto.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to a health insurance private exchange online platform.

One option for companies for providing health insurance to their employees is to offer health insurance options through a private exchange. There are several parties involved in this process. These include, for example, insurance brokers, group administrators, and consumers (e.g. employees).

Although some online platforms exist in this area, needs exist for improvement in this area. These, and other needs, are addressed by one or more aspects of the present invention.

SUMMARY OF THE INVENTION

The present invention includes many aspects and features. Moreover, while many aspects and features relate to, and are described in, the context of health insurance, the present invention is not limited to use only in this context, as will become apparent from the following summaries and detailed descriptions of aspects, features, and one or more embodiments of the present invention.

Accordingly, one aspect of the present invention relates to a method for facilitating employee selection of one or more health insurance products which includes maintaining, at an insurance portal platform, employer contribution information including a plurality of specific defined contribution amounts for each of a plurality of classes of health insurance products, including, for each class of product, an amount for enrollment of an employee, an amount for enrollment of an employee and his or her spouse, an amount for enrollment of an employee and his or her children, and an amount for enrollment of an employee and his family; and a lump sum defined contribution amount; displaying, to a user via an electronic display associated with an electronic device, a login interface for the insurance portal platform; receiving, from the user via one or more input devices associated with the electronic device, input corresponding to login credentials for the user; determining, by the insurance portal platform, that the user is an employee of the employer, and, based thereon, displaying, to the user via the electronic display, a plurality of specific defined contribution amounts for each of a plurality of classes of health insurance products, including, for each class of product, an amount for enrollment of an employee, an amount for enrollment of an employee and his or her spouse, an amount for enrollment of an employee and his or her children, and an amount for enrollment of an employee and his family; and displaying, to the user via the electronic display, information regarding a plurality of insurance products including, for each product, a coupon amount the cost of that product will be discounted based on a specific defined contribution amount for that class of health insurance product, and an estimated monthly cost after the coupon amount is applied; receiving, from the user via one or more input devices associated with the electronic device, input corresponding to selection of a health insurance product; displaying, to the user via the electronic display, information regarding the selected insurance product including an estimated cost of a plan including the selected health insurance product, a coupon amount the cost of the plan will be discounted based on a specific defined contribution amount for the class of the selected health insurance product, and a lump sum defined contribution amount the cost of the plan will be discounted, and an estimated monthly cost after the coupon amount and lump sum defined contribution amount are applied.

In a feature of this aspect, the plurality of classes of health insurance products includes major medical.

In a feature of this aspect, the plurality of classes of health insurance products includes dental.

In a feature of this aspect, the plurality of classes of health insurance products includes vision.

In a feature of this aspect, the plurality of classes of health insurance products includes accident.

In a feature of this aspect, the plurality of classes of health insurance products includes hospital.

In a feature of this aspect, the electronic display comprises a monitor.

In a feature of this aspect, the electronic display comprises a touchscreen.

In a feature of this aspect, the electronic device comprises a computer.

In a feature of this aspect, the electronic device comprises a tablet.

In a feature of this aspect, the electronic device comprises a phone.

In a feature of this aspect, the one or more input devices include a mouse.

In a feature of this aspect, the one or more input devices include a keyboard.

In a feature of this aspect, the one or more input devices include a touchscreen.

Another aspect relates to a method for facilitating employee selection of one or more health insurance products that includes displaying, to a user via an electronic display associated with an electronic device, a login interface for an insurance portal platform; receiving, from the user via one or more input devices associated with the electronic device, input corresponding to login credentials for the user; determining, by the insurance portal platform, that the user is an employee of the employer, and, based thereon, displaying, to the user via the electronic display, a plurality of specific defined contribution amounts for each of a plurality of classes of health insurance products, including, for each class of product, an amount for enrollment of an employee, an amount for enrollment of an employee and his or her spouse, an amount for enrollment of an employee and his or her children, and an amount for enrollment of an employee and his family; and displaying, to the user via the electronic display, information regarding a plurality of insurance products including, for each product, a coupon amount the cost of that product will be discounted based on a specific defined contribution amount for that class of health insurance product, and an estimated monthly cost after the coupon amount is applied; receiving, from the user via one or more input devices associated with the electronic device, input corresponding to selection of a health insurance product; displaying, to the user via the electronic display, information regarding the selected insurance product including an estimated cost of a plan including the selected health insurance product, a coupon amount the cost of the plan will be discounted based on a specific defined contribution amount for the class of the selected health insurance product, and a lump sum defined contribution amount the cost of the plan will be discounted, and an estimated monthly cost after the coupon amount and lump sum defined contribution amount are applied.

In a feature of this aspect, the plurality of classes of health insurance products includes major medical.

In a feature of this aspect, the plurality of classes of health insurance products includes dental.

In a feature of this aspect, the plurality of classes of health insurance products includes vision.

In a feature of this aspect, the plurality of classes of health insurance products includes accident.

Another aspect relates to a method for facilitating employee selection of one or more health insurance products which includes displaying, to a user via an electronic display, a plurality of specific defined contribution amounts for each of a plurality of classes of health insurance products, including, for each class of product, an amount for enrollment of an employee, an amount for enrollment of an employee and his or her spouse, an amount for enrollment of an employee and his or her children, and an amount for enrollment of an employee and his family; and displaying, to the user via the electronic display, information regarding a plurality of insurance products including, for each product, a coupon amount the cost of that product will be discounted based on a specific defined contribution amount for that class of health insurance product, and an estimated monthly cost after the coupon amount is applied; receiving, from the user via one or more input devices associated with the electronic device, input corresponding to selection of a health insurance product; displaying, to the user via the electronic display, information regarding the selected insurance product including an estimated cost of a plan including the selected health insurance product, a coupon amount the cost of the plan will be discounted based on a specific defined contribution amount for the class of the selected health insurance product, and a lump sum defined contribution amount the cost of the plan will be discounted, and an estimated monthly cost after the coupon amount and lump sum defined contribution amount are applied.

Another aspect relates to a method for allowing a broker to split commissions with one or more co-brokers. The method includes maintaining, at a broker portal platform, a list of brokers, each broker being associated with one or more insurance products; displaying, to a first one of the brokers via an electronic display associated with an electronic device, a broker portal interface for the broker portal platform which includes a search interface configured to allow the first broker to search for other brokers of the list of brokers; receiving, from the first broker via one or more input devices associated with the electronic device, input corresponding to indication of one or more search parameters; displaying, to the first broker via the electronic display, a broker portal interface for the broker portal platform including brokers of the maintained list of brokers which match the input search parameters; receiving, from the first broker via one or more input devices associated with the electronic device, input corresponding to selection of one or more brokers of the displayed brokers which match the input search parameters; communicating, to each of the selected brokers, an invitation to join as a co-broker for a particular client; receiving, from a second broker of the selected brokers, an indication of acceptance of the invitation; associating, at the broker portal platform, the second broker with the particular client; displaying, to the first one of the brokers via the electronic display associated with the electronic device, a broker portal interface for the broker portal platform which includes a list of brokers associated with the particular client, including the first broker and the second broker; and receiving, from the first broker via one or more input devices associated with the electronic device, input corresponding to a commission share for the second broker for the particular client.

In a feature of this aspect, the first broker is appointed to work with a first group of carriers, and the second broker is appointed to work with a second group of carriers. In a feature of this aspect, the input one or more search parameters comprise a location.

In a feature of this aspect, the input one or more search parameters comprise a carrier association.

In a feature of this aspect, the input one or more search parameters comprise a name.

In a feature of this aspect, the input one or more search parameters comprise a carrier association and a location.

Another aspect relates to a method for allowing a broker to split commissions with one or more co-brokers. The method includes maintaining, at a broker portal platform, a list of brokers, each broker being associated with one or more insurance products; displaying, to a first one of the brokers via an electronic display associated with an electronic device, a broker portal interface for the broker portal platform which includes a search interface configured to allow the first broker to search for other brokers of the list of brokers; receiving, from the first broker via one or more input devices associated with an electronic device, input corresponding to indication of one or more search parameters; displaying, to the first broker via an electronic display associated with an electronic device, a broker portal interface for the broker portal platform including brokers of the maintained list of brokers which match the input search parameters; receiving, from the first broker via one or more input devices associated with an electronic device, input corresponding to selection of one or more brokers of the displayed brokers which match the input search parameters; communicating, to each of the selected brokers, an invitation to join as a co-broker for a particular client; receiving, from a second broker of the selected brokers, an indication of acceptance of the invitation; associating, at the broker portal platform, the second broker with the particular client; displaying, to the first one of the brokers via an electronic display associated with an electronic device, a broker portal interface for the broker portal platform which includes a list of brokers associated with the particular client, including the first broker and the second broker; and receiving, from the first broker via one or more input devices associated with an electronic device, input corresponding to a commission share for the second broker for the particular client.

In a feature of this aspect, the first broker is appointed to work with a first group of carriers, and the second broker is appointed to work with a second group of carriers.

In a feature of this aspect, the input one or more search parameters comprise a location.

In a feature of this aspect, the input one or more search parameters comprise a carrier association.

In a feature of this aspect, the input one or more search parameters comprise a name.

Another aspect relates to one or more non-transitory computer readable media containing computer executable instructions for performing a method for allowing a broker to split commissions with one or more co-brokers. The method includes maintaining, at a broker portal platform, a list of brokers, each broker being associated with one or more insurance products; displaying, to a first one of the brokers via an electronic display associated with an electronic device, a broker portal interface for the broker portal platform which includes a search interface configured to allow the first broker to search for other brokers of the list of brokers; receiving, from the first broker via one or more input devices associated with the electronic device, input corresponding to indication of one or more search parameters; displaying, to the first broker via the electronic display, a broker portal interface for the broker portal platform including brokers of the maintained list of brokers which match the input search parameters; receiving, from the first broker via one or more input devices associated with the electronic device, input corresponding to selection of one or more brokers of the displayed brokers which match the input search parameters; communicating, to each of the selected brokers, an invitation to join as a co-broker for a particular client; receiving, from a second broker of the selected brokers, an indication of acceptance of the invitation; associating, at the broker portal platform, the second broker with the particular client; displaying, to the first one of the brokers via the electronic display associated with the electronic device, a broker portal interface for the broker portal platform which includes a list of brokers associated with the particular client, including the first broker and the second broker; and receiving, from the first broker via one or more input devices associated with the electronic device, input corresponding to a commission share for the second broker for the particular client.

Another aspect relates to a method for facilitating employee selection of one or more health insurance products comprising maintaining, at an insurance portal platform, information regarding a plurality of health insurance products available for employees of an employer; displaying, to a user via an electronic display associated with an electronic device, a login interface for the insurance portal platform; receiving, from the user via one or more input devices associated with the electronic device, input corresponding to login credentials for the user; determining, by the insurance portal platform, that the user is an employee of the employer, and, based thereon, determining one or more health insurance products which require an active enrollment decision by the user; preloading, into a user shopping cart of the insurance portal platform for the user, the one or more health insurance products determined to require an active enrollment decision by the user; receiving, from the user via one or more input devices associated with the electronic device, input corresponding to accessing the shopping cart; and displaying, to the user via the electronic display, the shopping cart which includes the one or more health insurance products determined to require an active enrollment decision by the user.

Another aspect relates to a method for facilitating employee selection of one or more health insurance products comprising maintaining, at an insurance portal platform, information regarding a plurality of health insurance products available for employees of an employer; displaying, to a user via an electronic display associated with an electronic device, a login interface for the insurance portal platform; receiving, from the user via one or more input devices associated with the electronic device, input corresponding to login credentials for the user; determining, by the insurance portal platform, that the user is an employee of the employer, and, based thereon, determining one or more health insurance products which require an active enrollment decision by the user; preloading, into a user shopping cart of the insurance portal platform for the user, the one or more health insurance products determined to require an active enrollment decision by the user; receiving, from the user via one or more input devices associated with the electronic device, input indicating a desire to check out; and displaying, to the user via the electronic display, the shopping cart which includes the one or more health insurance products determined to require an active enrollment decision by the user.

Another aspect relates to one or more non-transitory computer readable media containing computer executable instructions for performing a method for facilitating employee selection of one or more health insurance products comprising maintaining, at an insurance portal platform, information regarding a plurality of health insurance products available for employees of an employer; displaying, to a user via an electronic display associated with an electronic device, a login interface for the insurance portal platform; receiving, from the user via one or more input devices associated with the electronic device, input corresponding to login credentials for the user; determining, by the insurance portal platform, that the user is an employee of the employer, and, based thereon, determining one or more health insurance products which require an active enrollment decision by the user; preloading, into a user shopping cart of the insurance portal platform for the user, the one or more health insurance products determined to require an active enrollment decision by the user; receiving, from the user via one or more input devices associated with the electronic device, input corresponding to accessing the shopping cart; and displaying, to the user via the electronic display, the shopping cart which includes the one or more health insurance products determined to require an active enrollment decision by the user.

Another aspect relates to a method for allowing a broker to selectively hide commission information for presentation of insurance plan information to a client, the method comprising displaying, to a broker on an electronic display associated with an electronic device, a broker portal interface in a broker display mode including health insurance plan information for a client of the broker, broker commission information for the broker, and a toggle interface element configured to allow the broker to toggle to a face-to-face display mode; and receiving, from the broker via one or more input devices associated with the electronic device, input corresponding to engagement of the toggle interface element; and displaying, on the electronic display in response to the input corresponding to engagement of the toggle interface element, a broker portal interface in the face-to-face display mode including health insurance plan information for a client of the broker, and a toggle interface element configured to allow the broker to toggle to the broker display mode, wherein the broker portal interface in the face-to-face display mode does not include broker commission information.

In a feature of this aspect, the broker commission information comprises commission split information.

Another aspect relates to a method comprising displaying, to a broker via an electronic display associated with an electronic device, a broker portal interface configured to toggle between a first broker display mode and a second face-to-face display mode, wherein the broker display mode includes health insurance plan information for a client of the broker, broker commission information for the broker, and a toggle interface element configured to allow the broker to toggle to the face-to-face display mode; and the face-to-face display mode includes health insurance plan information for a client of the broker, and a toggle interface element configured to allow the broker to toggle to the broker display mode; wherein the face-to-face display mode does not include broker commission information; receiving, from the broker via one or more input devices associated with the electronic device, input corresponding to engagement of the toggle interface element configured to allow the broker to toggle to the face-to-face display mode; and displaying, on the electronic display in response to the input corresponding to engagement of the toggle interface element configured to allow the broker to toggle to the face-to-face display mode, a broker portal interface in the face-to-face display mode.

In a feature of this aspect, the electronic display comprises a monitor.

In a feature of this aspect, the electronic display comprises a touchscreen.

In a feature of this aspect, the electronic device comprises a computer.

In a feature of this aspect, the electronic device comprises a tablet.

In a feature of this aspect, the one or more input devices include a mouse.

In a feature of this aspect, the one or more input devices include a keyboard.

In a feature of this aspect, the one or more input devices include a touchscreen.

In a feature of this aspect, the broker commission information comprises commission split information.

Another aspect relates to one or more non-transitory computer readable media containing computer executable instructions for performing a method for allowing a broker to selectively hide commission information for presentation of insurance plan information to a client, the method comprising displaying, to a broker on an electronic display associated with an electronic device, a broker portal interface in a broker display mode including health insurance plan information for a client of the broker, broker commission information for the broker, and a toggle interface element configured to allow the broker to toggle to a face-to-face display mode; and receiving, from the broker via one or more input devices associated with the electronic device, input corresponding to engagement of the toggle interface element; and displaying, on the electronic display in response to the input corresponding to engagement of the toggle interface element, a broker portal interface in the face-to-face display mode including health insurance plan information for a client of the broker, and a toggle interface element configured to allow the broker to toggle to the broker display mode, wherein the broker portal interface in the face-to-face display mode does not include broker commission information.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein, FIG. 1 illustrates an exemplary broker interface of a platform in accordance with one or more preferred implementations;

FIG. 7 illustrates an overview interface for a group;

FIGS. 8-9 illustrate an exemplary interface for allowing a broker user to set up a plan year for a group;

FIGS. 10A-11D illustrate exemplary interfaces related to broker assignment and commission splits;

FIG. 13 illustrates an exemplary interface presenting plan options for medical coverage for a plan year;

FIG. 15 illustrates an interface presenting a summary of selected plans;

FIG. 17 illustrates an exemplary interface which provides an overview of a created plan year and provides a broker user the ability to submit the plan year to a group administrator for approval;

FIG. 19 illustrates an overview page which presents a group overview including plan year information;

FIG. 20 illustrates an exemplary interface which allows a group administrator user to search for employees and review employee information;

Figure 21:
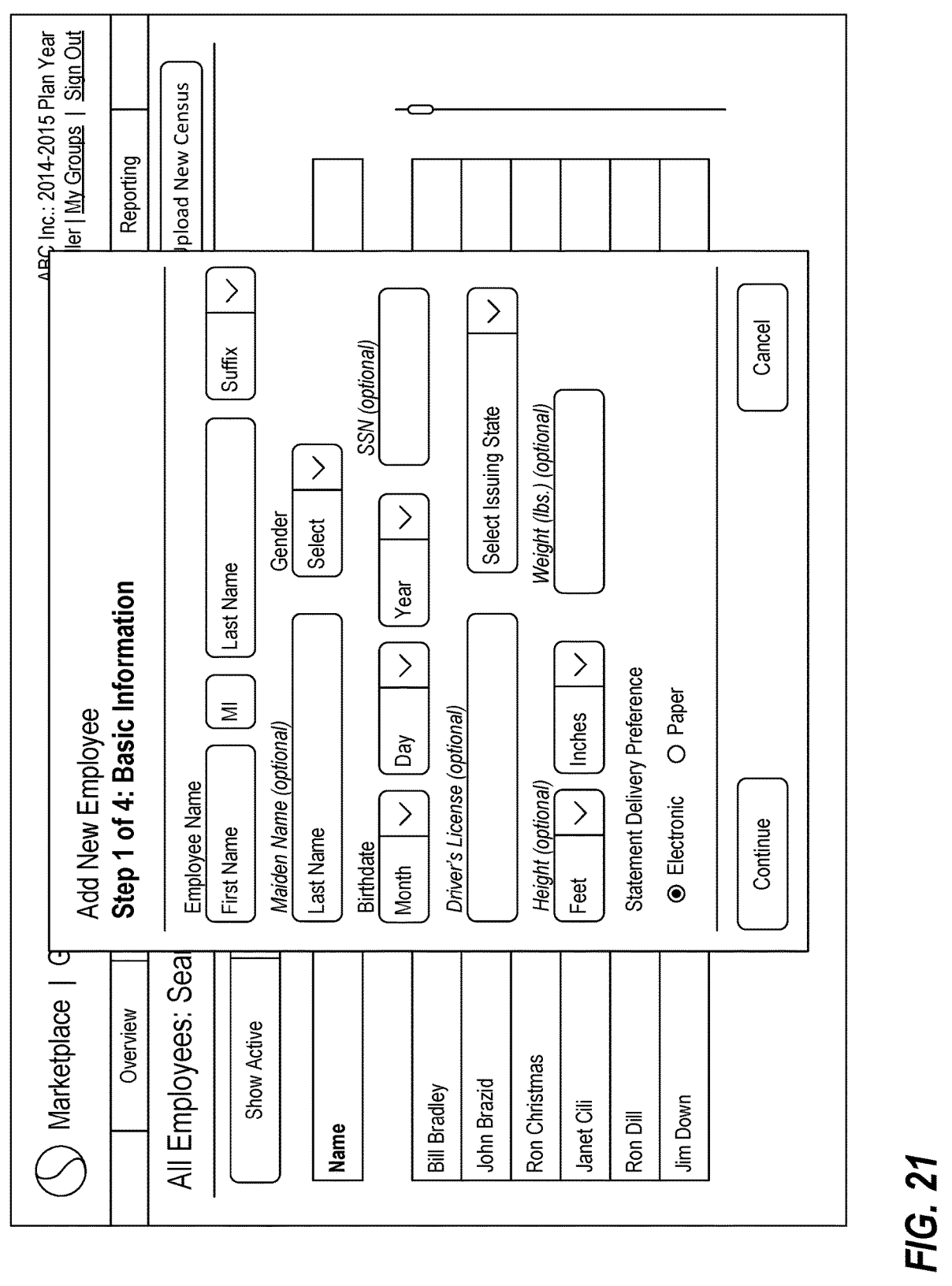
Figure 22:
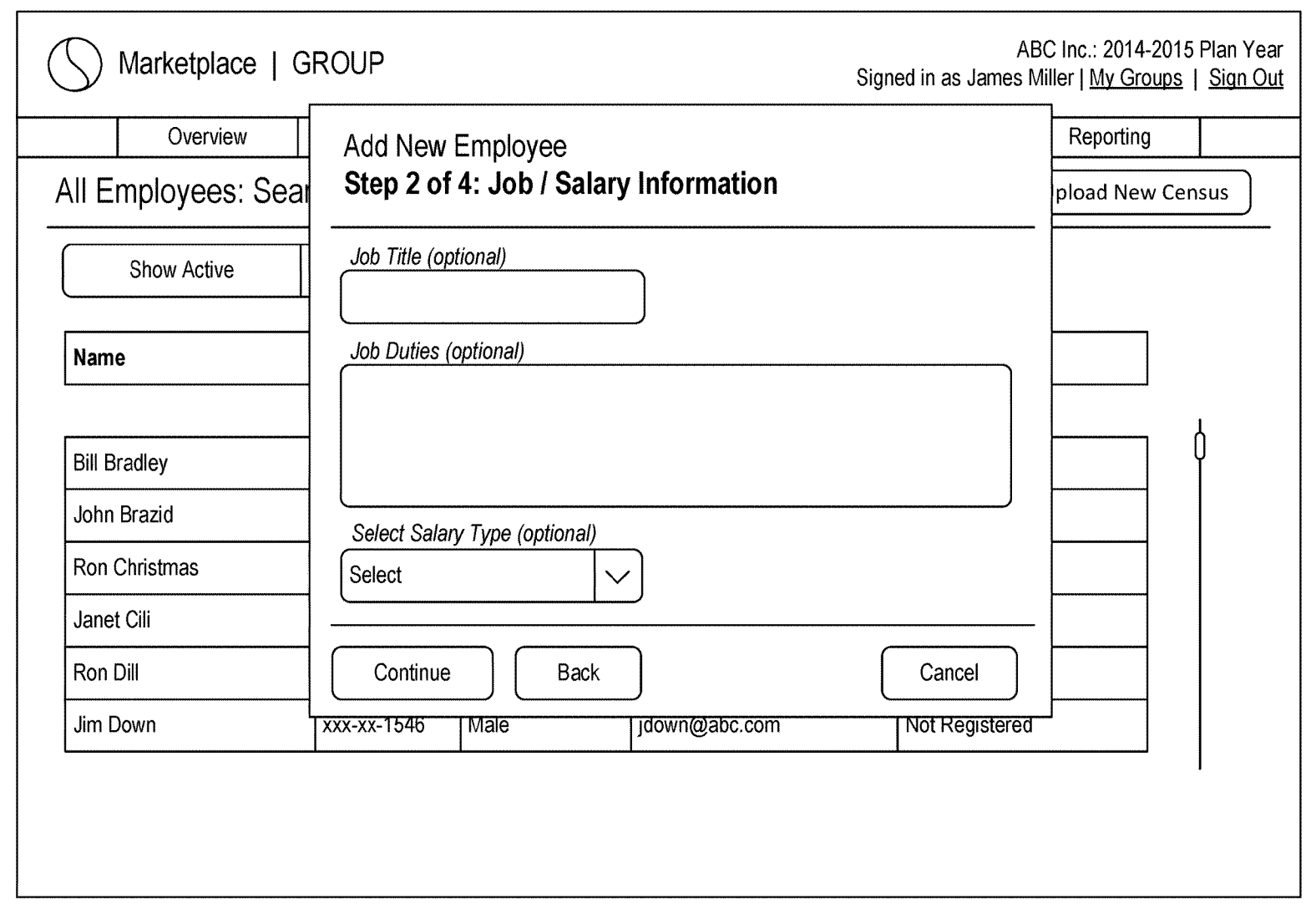
Figure 24:
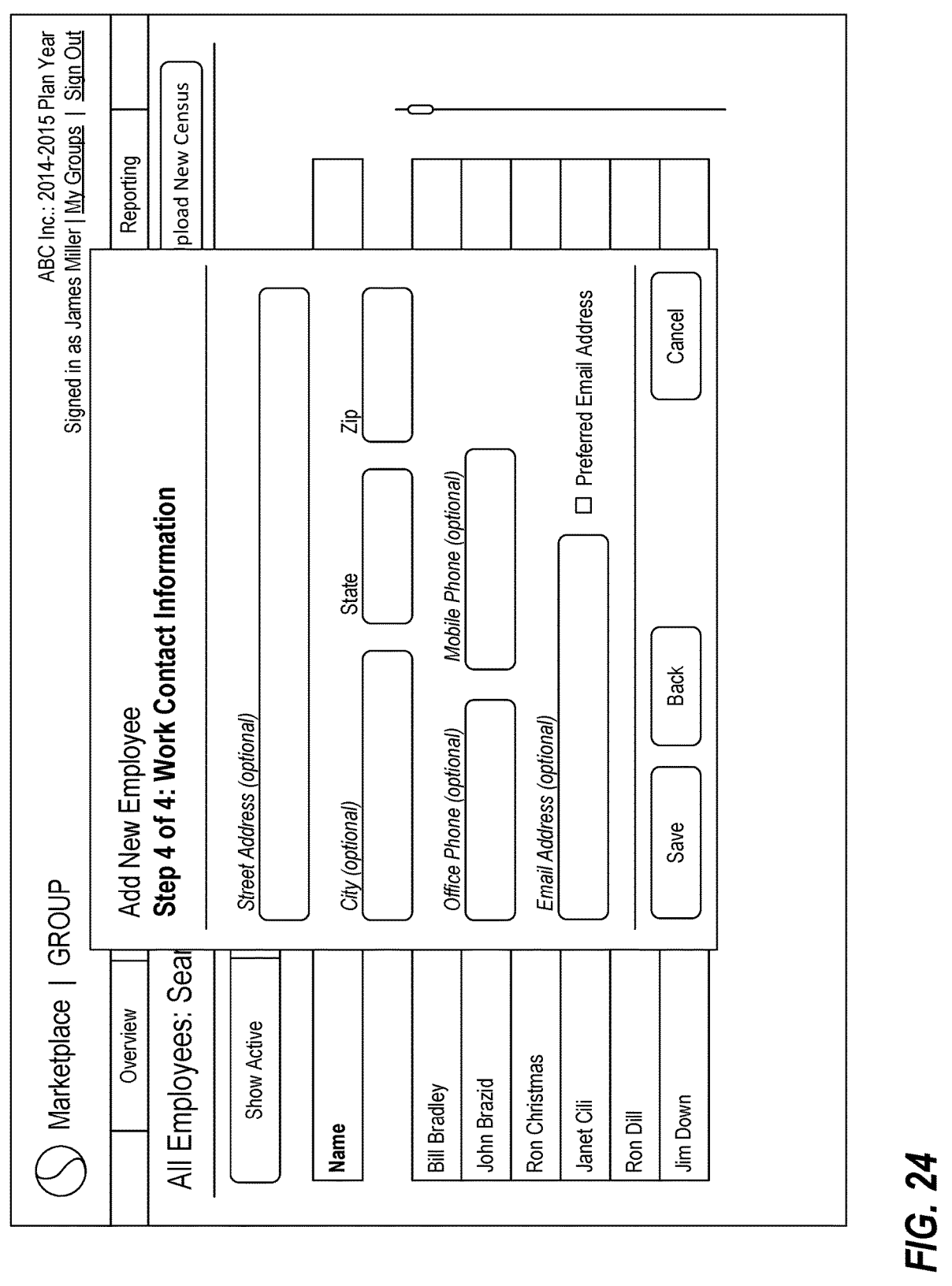

FIGS. 21-24 illustrate exemplary interfaces for a workflow for adding a new employee;

FIG. 25 illustrates an exemplary employee information interface;

FIGS. 26-28 illustrate a workflow for terminating an employee;

FIG. 29 illustrates an interface for rehiring an employee;

FIG. 30 illustrates an interface for reviewing and editing dependent information for an employee;

FIGS. 31A-B illustrate interfaces for reviewing and editing qualifying events for an employee;

FIG. 32 illustrates an interface which allows a group administrator user to review a coverage summary for an employee;

FIG. 33 illustrates an interface which allows a group administrator user to review and edit contribution amounts for all employees for the group;

FIG. 34 illustrates an interface which allows a group administrator user to review product/plan information for a group;

FIG. 36 illustrates an exemplary interface which allows for the review and editing of group administrators;

FIG. 37 illustrates an exemplary reporting interface which allows a group administrator user to access a payroll report, demographic report, and enrollment report;

FIGS. 40-41 illustrate interfaces which provide an estimate of plan costs;

FIG. 42 illustrates exemplary specific employer contribution, or coupon, amounts for various product and coverage combinations;

FIG. 43 illustrates an interface including exemplary coupons for insurance plans;

FIG. 44 illustrates an exemplary interface which provides plan information to an employee user for selection of a plan;

FIG. 45 illustrates an interface which allows an employee user to add additional information for filtering plans;

FIG. 46 illustrates an interface configured to allow an employee user to compare plans;

FIG. 47 illustrates functionality related to a cost estimate for selected plans;

FIG. 48 illustrates an interface including a listing of selected plans and cost estimates therefor;

FIG. 49 illustrates an interface forming part of a consolidated check out process flow;

FIG. 50 illustrates an interface including exemplary product bundles;

DETAILED DESCRIPTION

Figure 2:
FIGS. 2-6 illustrate exemplary interfaces for creation of a new group.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In accordance with one or more preferred implementations, a health insurance exchange platform is configured for use by brokers, group administrators, and consumers (e.g. employees).

Preferably, broker users can utilize the platform to create and manage groups, e.g. companies they manage insurance options for. In order to utilize the platform to create and manage groups, a broker user first needs to sign in to the platform with a user name and password.

Figure 1:
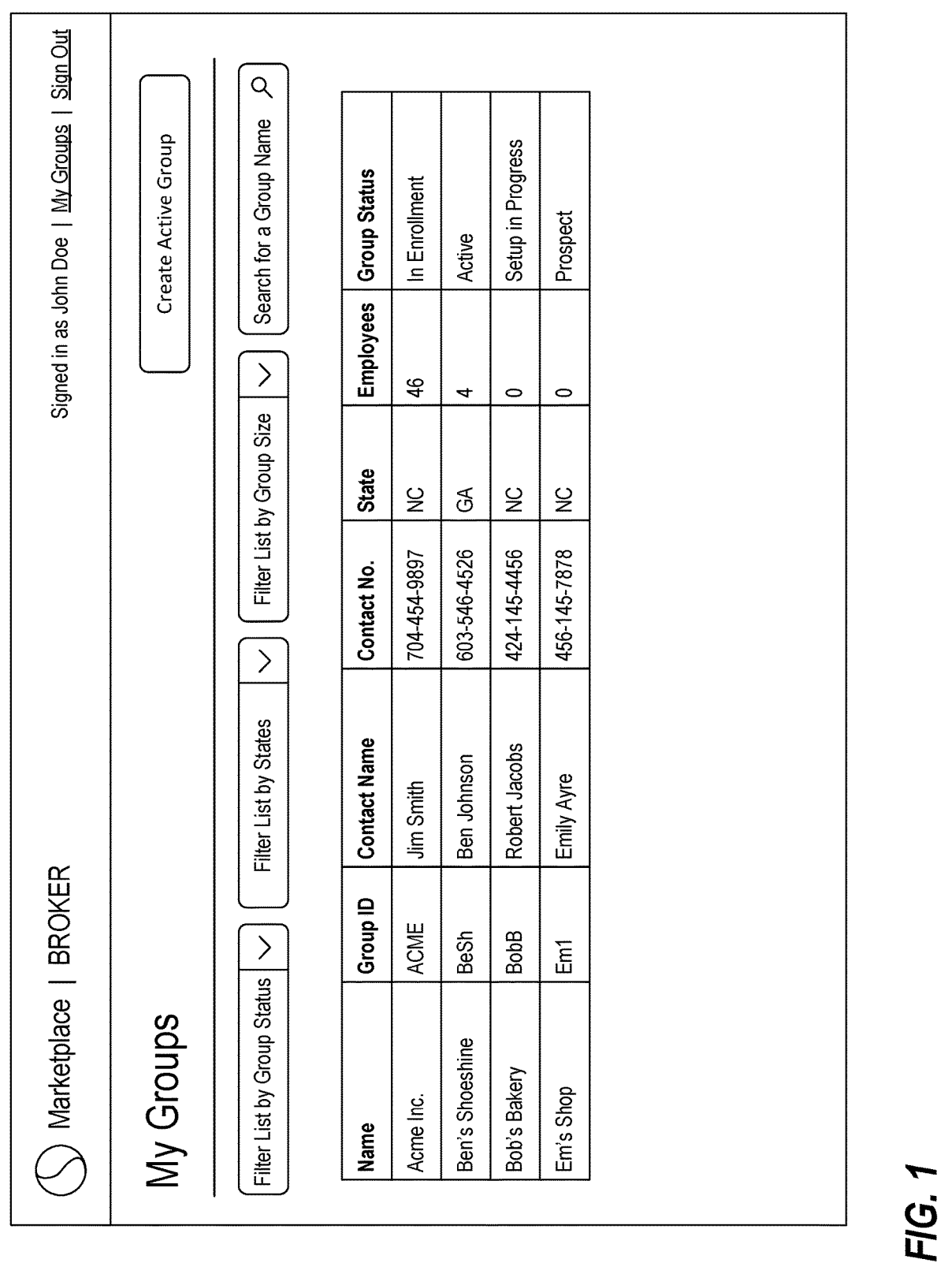

FIG. 1 illustrates an exemplary broker interface of a platform in accordance with one or more preferred implementations. The interface displays a list of groups managed by a broker, and allows the broker user to search for a particular group or filter the groups by various criteria, such as status, state, and size.

The interface further allows a broker user to create a new group using a "Create Active Group" button. FIGS. 2-6 illustrate exemplary interfaces for creation of a new group.

Figure 4:
Figure 5:
Figure 6:

In particular, a first interface prompts a broker user for entry of a group name and address, as illustrated in FIG. 2, a second interface prompts a broker user for entry of group administrators, as illustrated in FIG. 4, and a third interface prompts a broker user for entry of billing information, as illustrated in FIG. 5.

Figure 3:

In an exemplary use case, a broker user named John Doe uses this interface to create a new group named ABC, Inc., as illustrated in FIG. 3. The broker user specifies a single group administrator, James Miller, as illustrated in FIG. 5.

Following creation of a new group, or upon selecting a group, a broker user is presented with an overview interface for a group. An exemplary such interface is illustrated in FIG. 7. The group overview interface preferably displays information for the group, as well as recent activities associated with the group.

Preferably, if a plan year has not been set up for the group, the interface will indicate this, as illustrated in FIG. 7, and prompt a broker user to set up a plan year for the group.

FIG. 8 illustrates an exemplary interface for allowing a broker user to set up a plan year for a group. As illustrated in FIG. 8, a basic information pane allows a broker user to input enrollment dates and coverage dates for the plan year, and input census information either by uploading a file containing census data, or by inputting census summary data in advance of later uploading of a census file by a group administrator. In an exemplary use case, the John Doe broker user previously mentioned inputs appropriate dates and uploads a census file, as illustrated in FIG. 9.

Figure 10A:
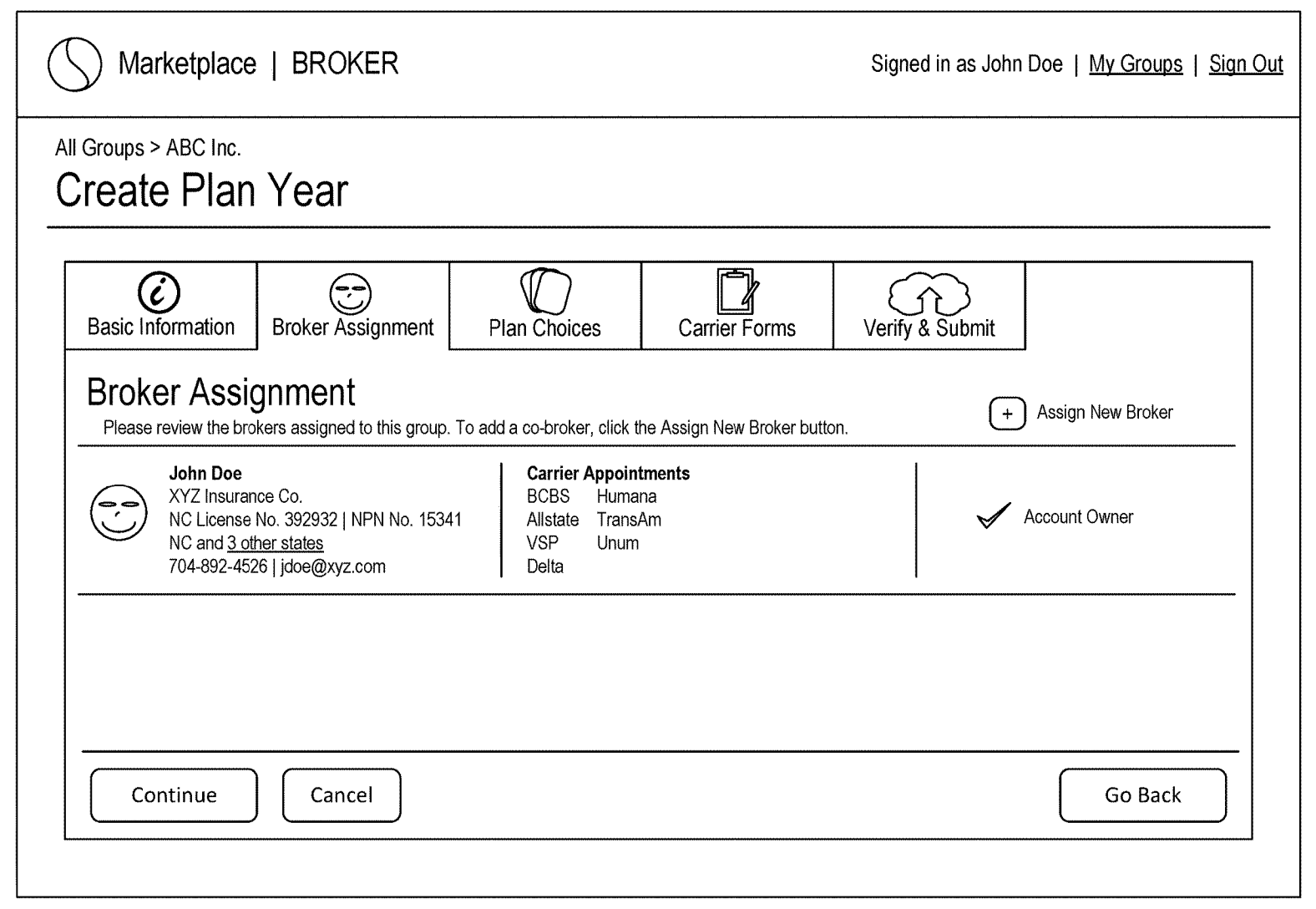

Next, as part of setting up a plan year, a broker user is preferably presented with a broker assignment interface, as illustrated in FIG. 10A. Preferably, the broker assignment interface allows a broker user to assign one or more additional brokers via use of an "Assign New Broker" button.

FIG. 10B illustrates an exemplary interface for searching for other brokers to add. The interface preferably allows a broker user to search for other brokers based on, for example, a state of licensure of other brokers, products or carriers other brokers are associated with, or a name of other brokers.

If a broker user selects another broker to add to the plan year, an invitation will preferably be sent to the other broker, e.g. via email or via a notification communicated through the platform, and the additional broker will be indicated on the broker assignment pane, as illustrated in FIG. 11A. Preferably, an indication of whether or not the additional broker has accepted the invitation to serve as a broker for the group is displayed on the broker assignment pane, as illustrated in FIG. 11A.

Figure 11B:
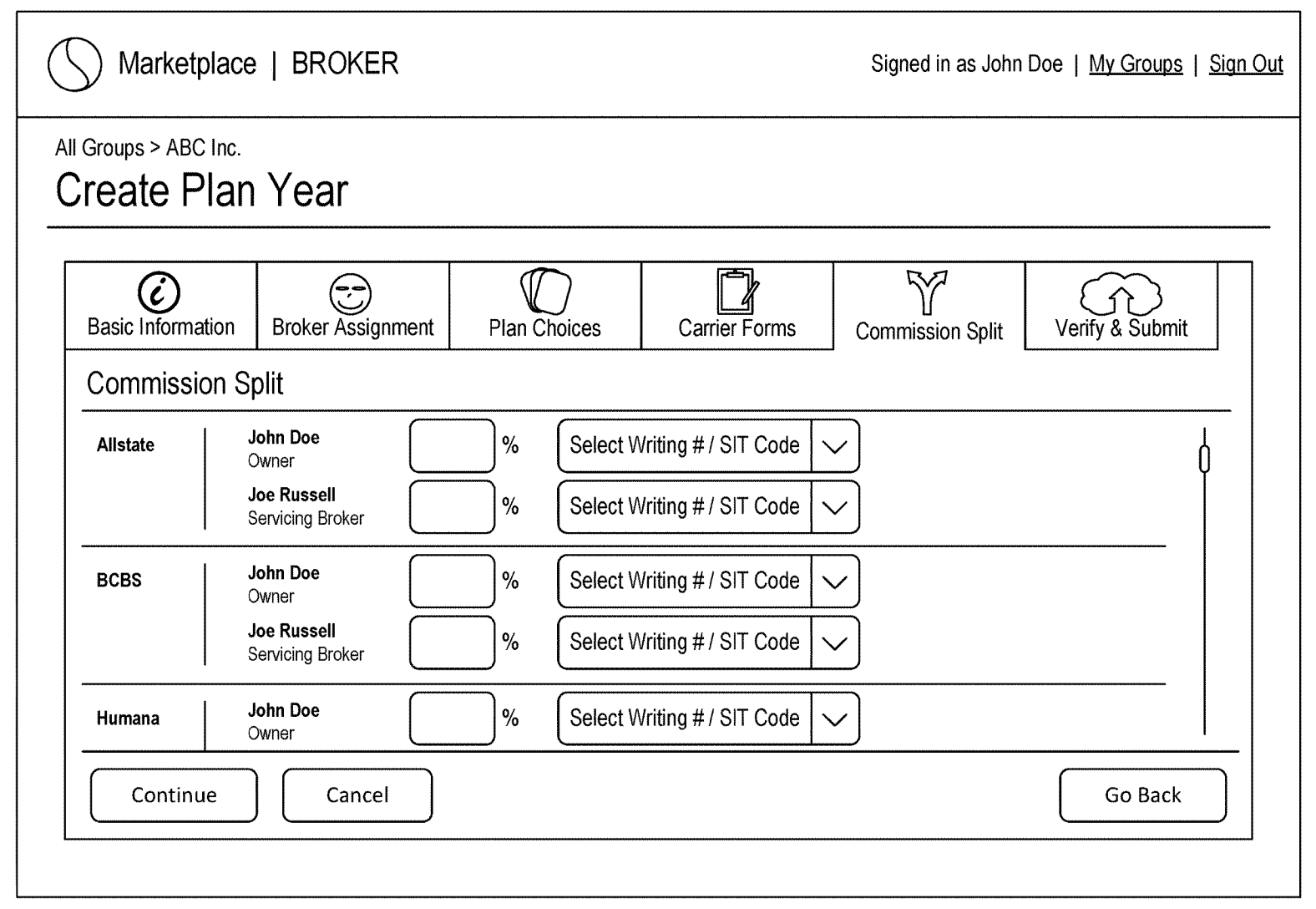

In one or more preferred implementations, an interface includes a pane for allowing a broker use to specify a commission split for each broker associated with a plan year. FIG. 11B illustrates an exemplary such interface which allows a broker use to specify a commission split for each carrier forming part of the plan year. In one or more preferred implementations, a commission split can be specified at a plan level, carrier level, and/or product level.

Figure 11C:
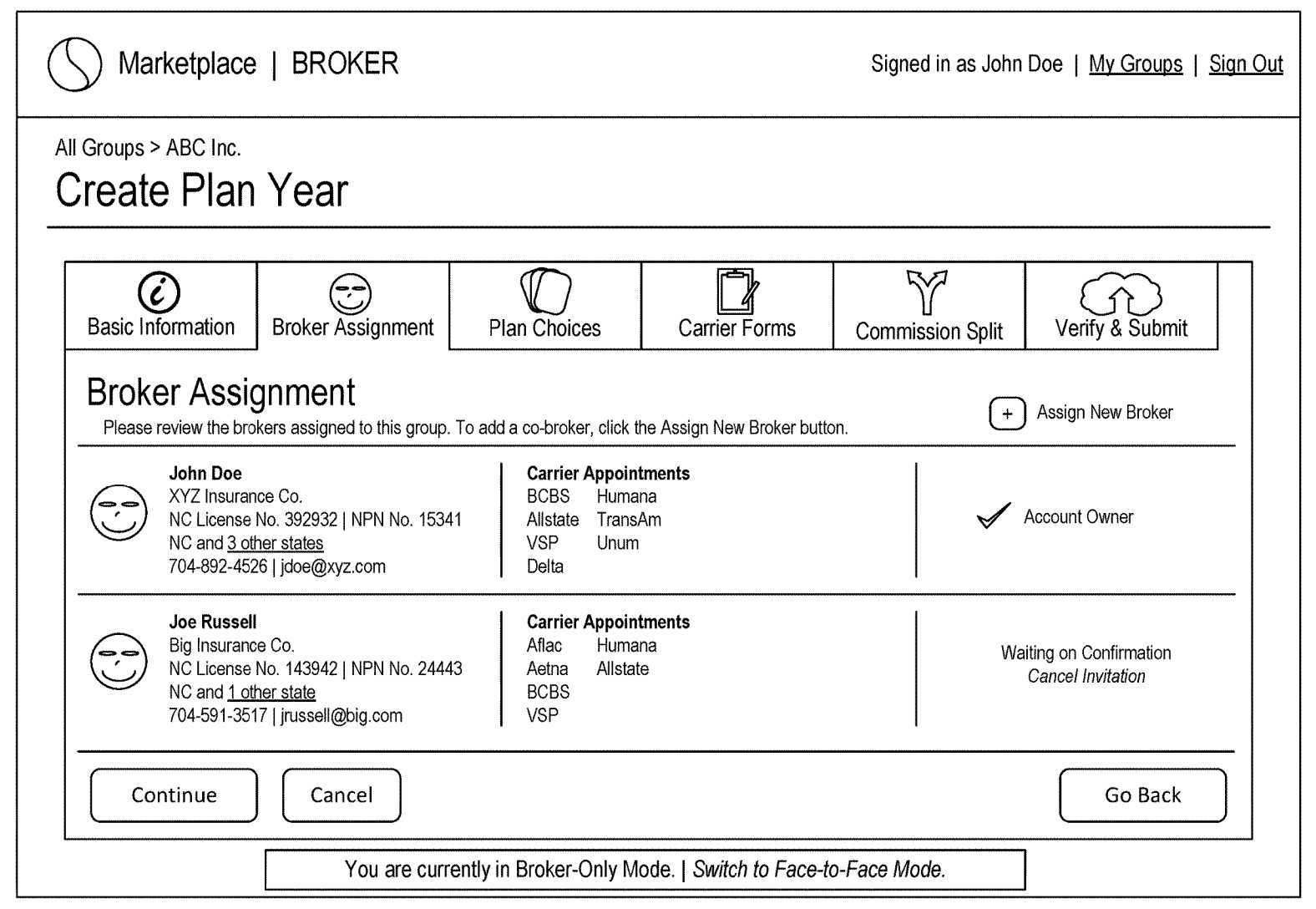

In one or more preferred implementations, an interface is configured to be toggled between a broker-only mode, configured for viewing by a broker user, and a face-to-face mode, configured for use by a broker user in sharing his screen with one or more clients or customers. For example, in one or more preferred implementations, a face-to-face mode may omit display of commission split information. FIG. 11C illustrates an exemplary interface in a broker-only mode, and FIG. 11D illustrates the exemplary interface in a face-to-face mode.

Figure 12:
FIG. 12 illustrates an exemplary interface which allows a broker user to select carriers for which products may be offered for each of a variety of plan types.

Next, as part of setting up a plan year, a broker user is preferably presented with one or more interfaces which allow for selection of one or more carriers and products to offer as part of the plan year. FIG. 12 illustrates an exemplary interface which allows a broker user to select carriers for which products may be offered for each of a variety of plan types. In one or more preferred implementations, the list of carriers is populated based on the carriers available for the brokers associated with the plan year. In one or more preferred implementations, the plan types are populated based on products available from those carriers.

Figure 13:
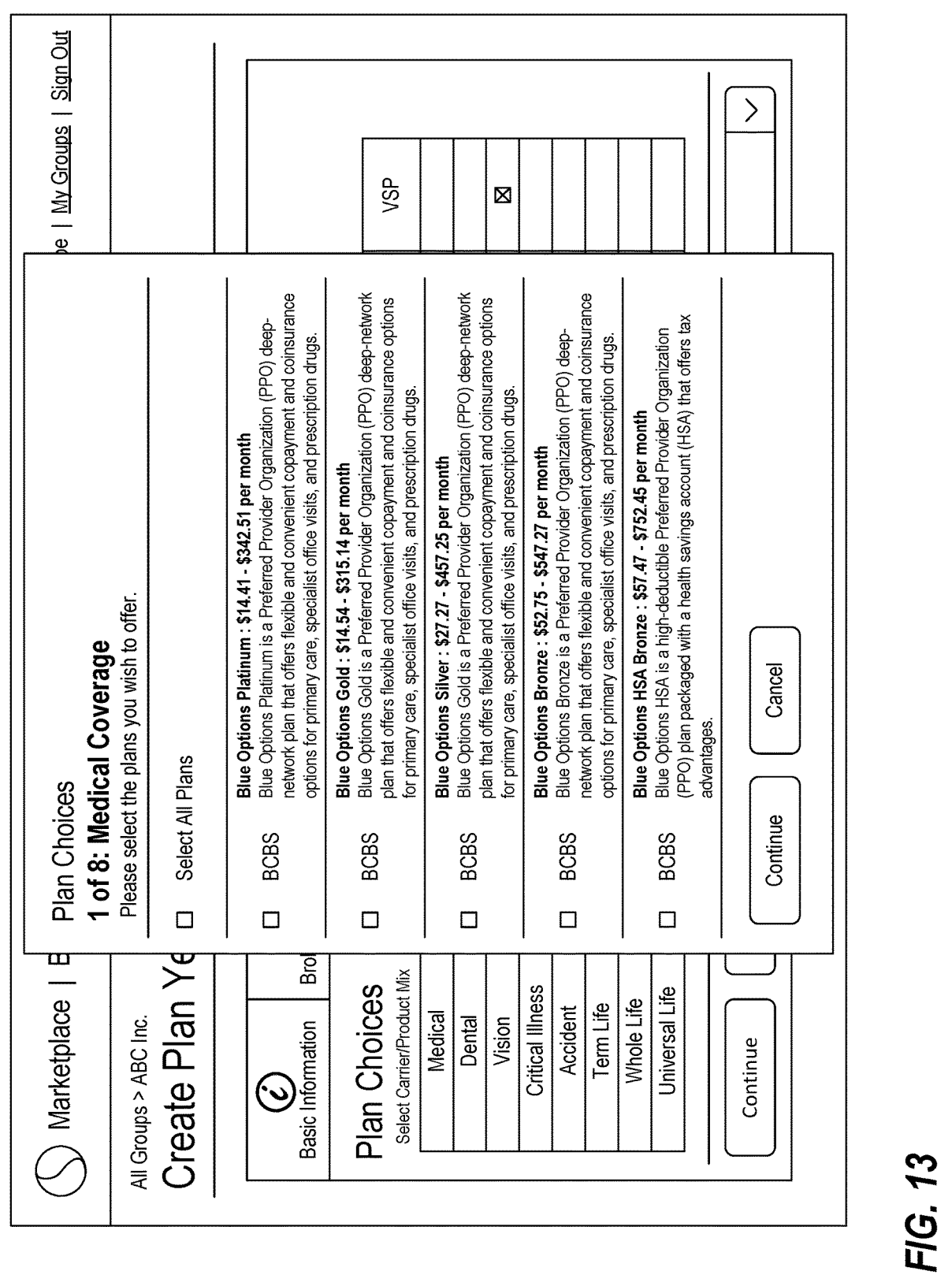

In one or more preferred implementations, after selecting carriers to be available under the plan year, a broker user is presented with a plurality of interfaces for selecting specific products, or plans, that will be available for the plan year. FIG. 13 illustrates an exemplary such interface presenting plan options for medical coverage for a plan year. Preferably, after selecting one or more plans for medical coverage to be available under the plan, a broker user is presented with a similar interface for each plan type.

Figure 14:
FIG. 14 illustrates an exemplary defined contribution interface.

In one or more preferred implementations, a broker user is thereafter presented with a defined contribution interface. Preferably, the defined contribution interface allows a user to specify, for one or more carriers or products, a minimum portion covered by a defined contribution, a default defined contribution amount for all employees, and an order of defined contribution priority for different plan types. FIG. 14 illustrates an exemplary defined contribution interface.

Figure 15:
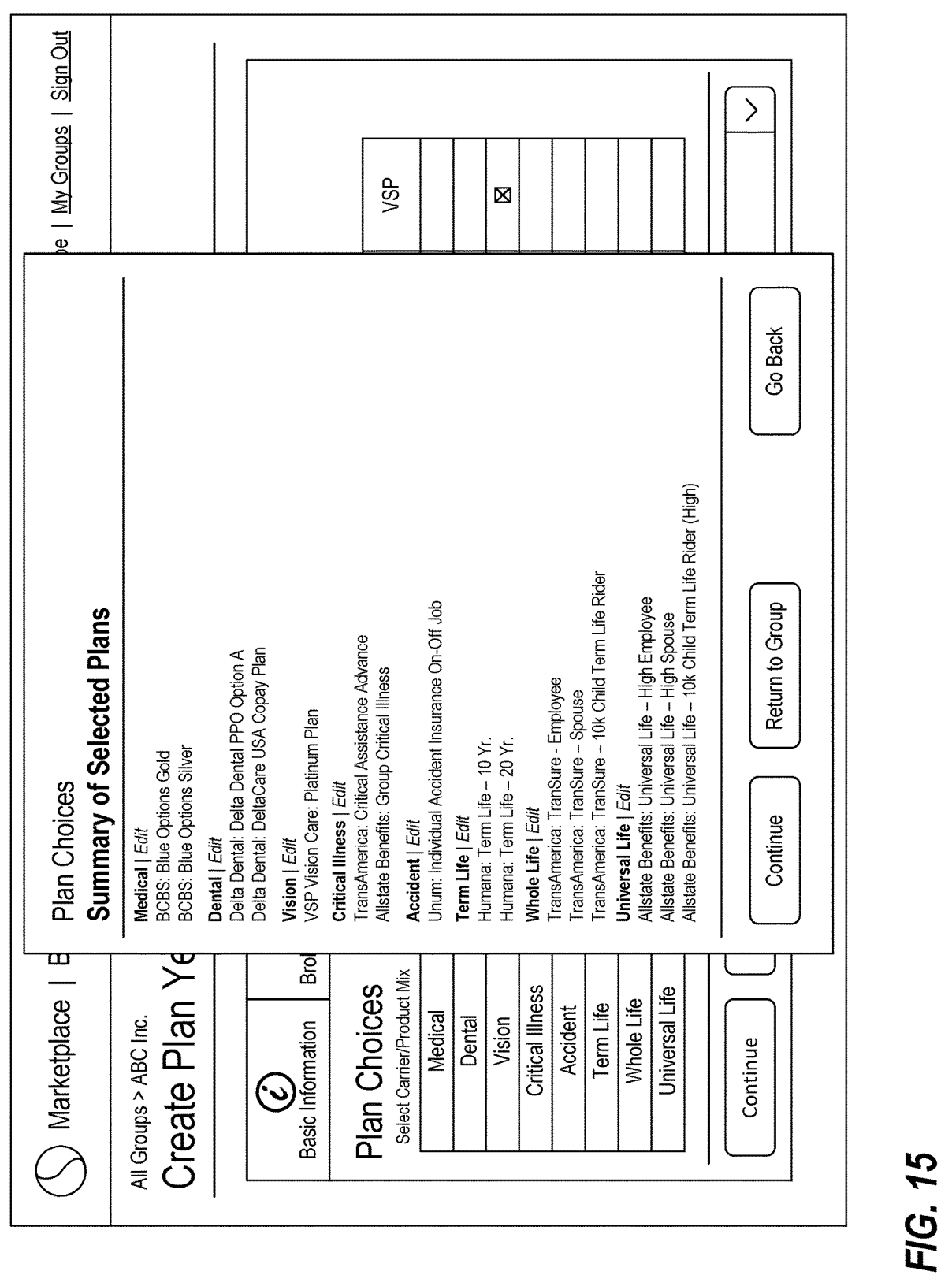

In one or more preferred implementations, after selecting specific products or plans that will be available for a plan year, a broker user is presented with a summary of selected plans, as illustrated in FIG. 15.

Figure 16:
FIG. 16 illustrates an exemplary interface which tracks, for each carrier associated with a plan, when forms are completed, when the group has provided approval, when the forms are submitted to the carrier, and when the carrier has provided approval.

In one or more preferred implementations, an interface includes a pane for allowing a broker use to track and manage carrier forms for each selected plan. FIG. 16 illustrates an exemplary such interface which tracks, for each carrier associated with a plan, when forms are completed, when the group has provided approval, when the forms are submitted to the carrier, and when the carrier has provided approval.

Once a broker user has completed the carrier forms for each carrier associated with the plan year, the broker user can submit the plan year to an administrator of the group for approval. FIG. 17 illustrates an exemplary interface which provides an overview of a created plan year and provides a broker user the ability to submit the plan year to a group administrator for approval.

Returning to the use case involving broker user John Doe previously described, because John Doe specified James Miller as the group administrator for the group, the interface allows John Doe to submit the plan year for approval by James Miller.

Figure 18:
FIG. 18 illustrates an exemplary interface allowing for review of company information, employee census information, plan choices, and carrier forms.
Figure 23:

Thereafter, James Miller can log in to the platform as a group administrator user and review, update, and approve the created plan year. In particular, once a group administrator user authenticates with the portal, he can review and confirm company information, employee census information, plan choices, and carrier forms. FIG. 18 illustrates an exemplary interface allowing for such review. As illustrated, the group administrator user has already reviewed and signed all applicable carrier documents, so this is indicated on the interface.

In one or more preferred implementations, a platform further allows a group administrator user to access and edit plan year information for a plan year. FIG. 19 illustrates an overview page which presents a group overview including plan year information.

Preferably, the platform further includes functionality allowing a group administrator to review and edit employee information for the group. FIG. 20 illustrates an exemplary interface which allows a group administrator user to search for employees and review employee information.

In one or more preferred implementations, the interface further allows a group administrator user to add a new employee. FIGS. 21-24 illustrate exemplary interfaces for a workflow for adding a new employee.

Figure 25:
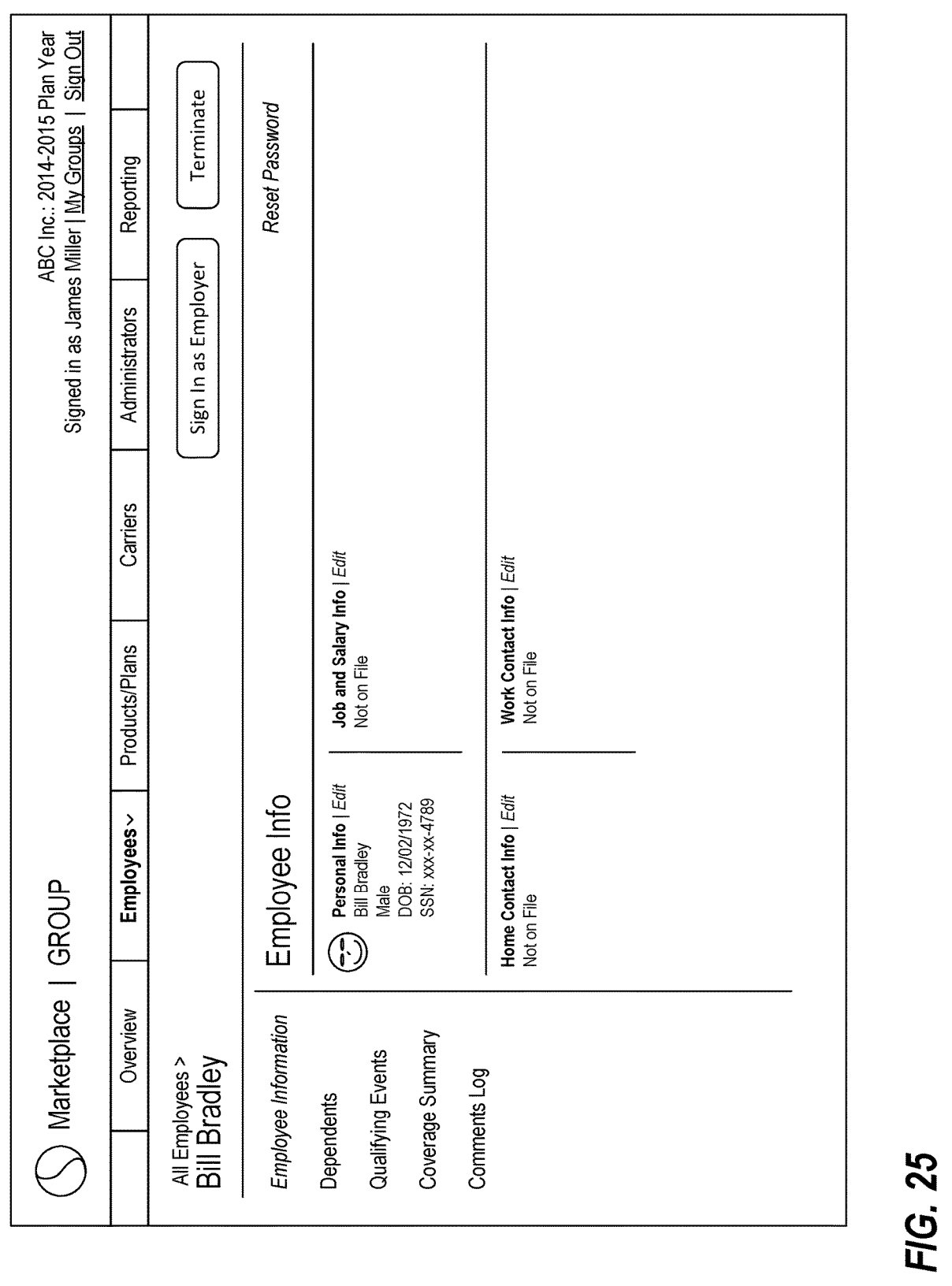

Preferably, a group administrator user can review and edit information for each employee via an employee information interface accessed either via searching for an employee, or upon creating a new employee. FIG. 25 illustrates an exemplary such interface.

Figure 26:
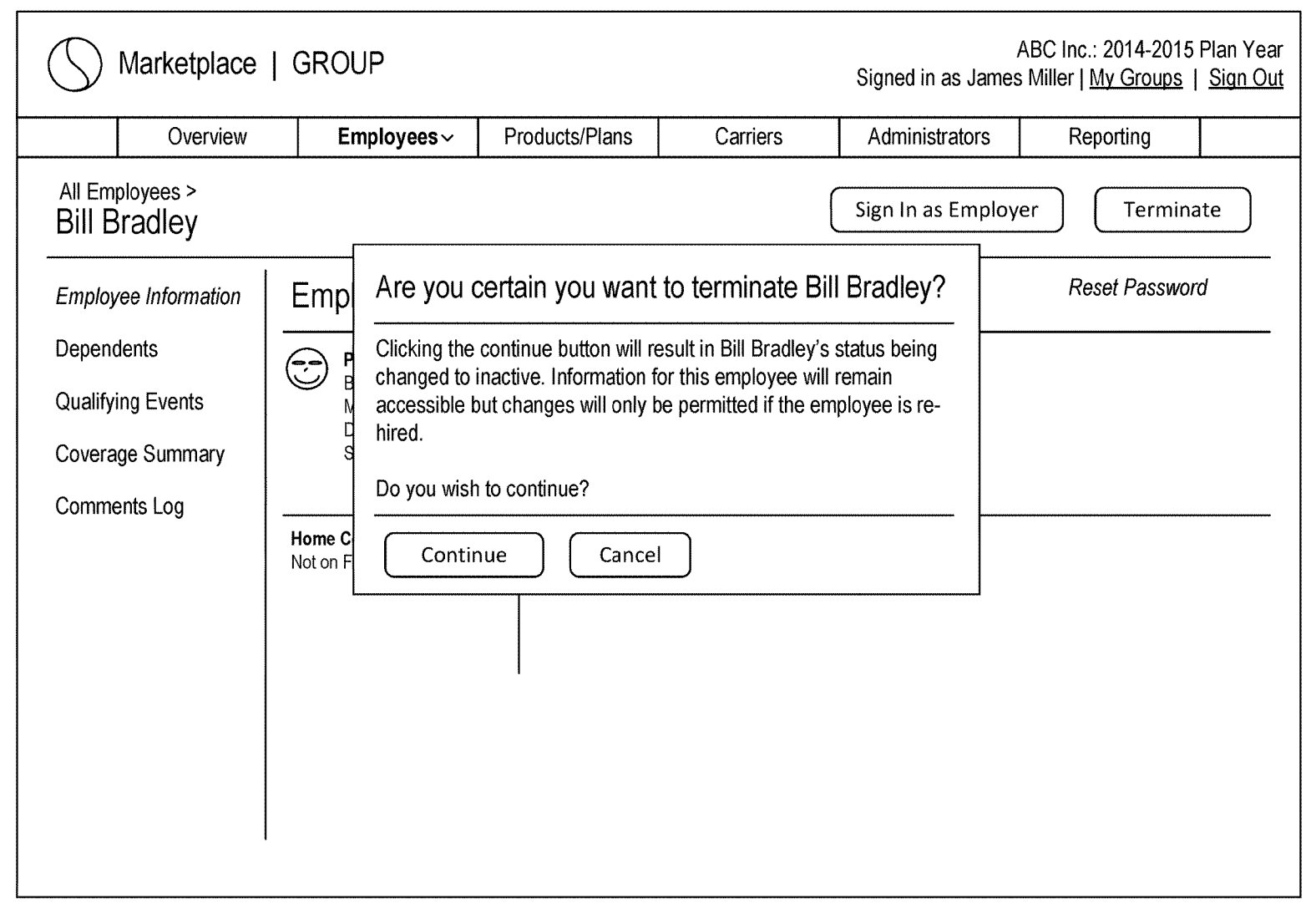
Figure 27:
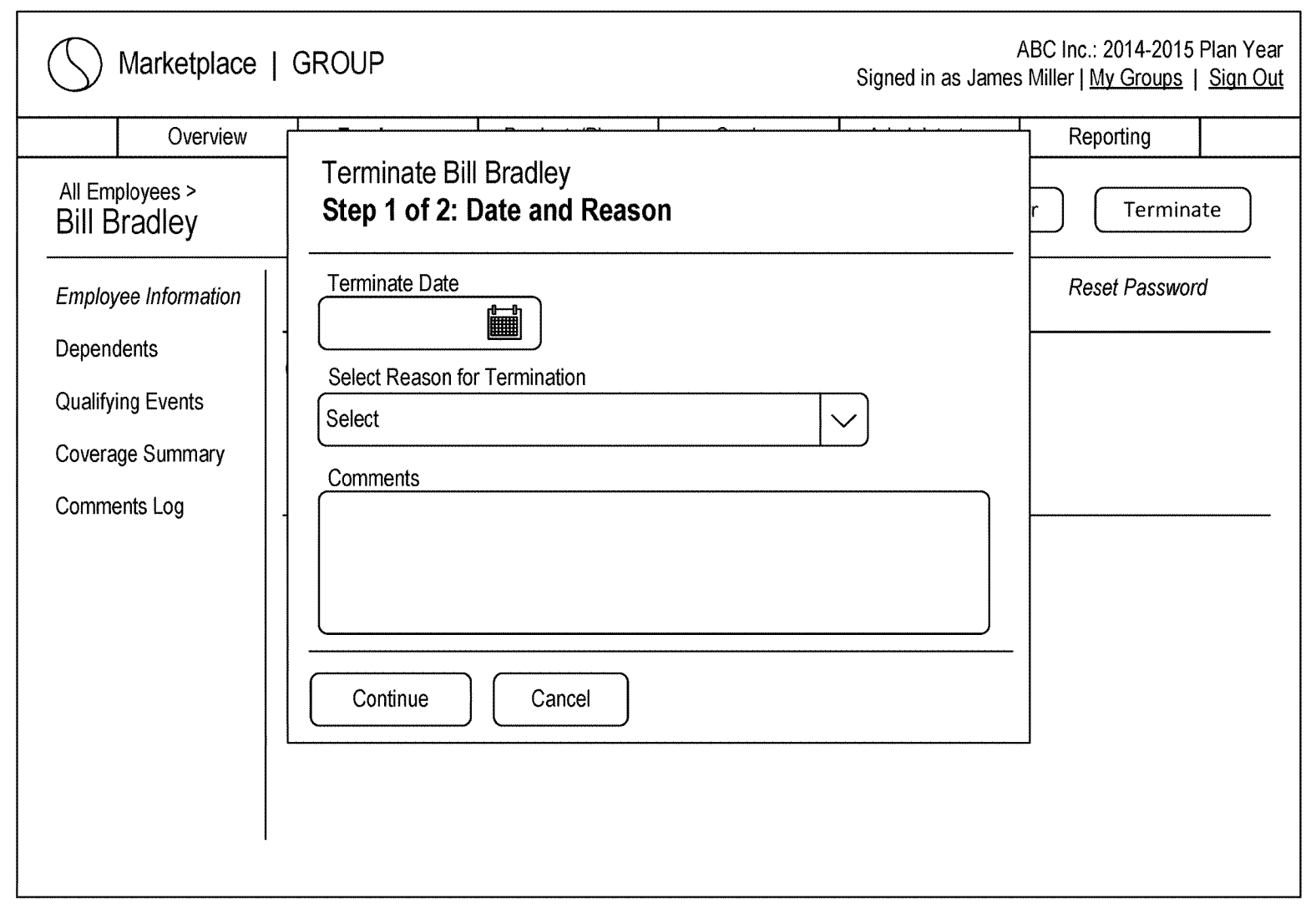
Figure 28:
Figure 29:
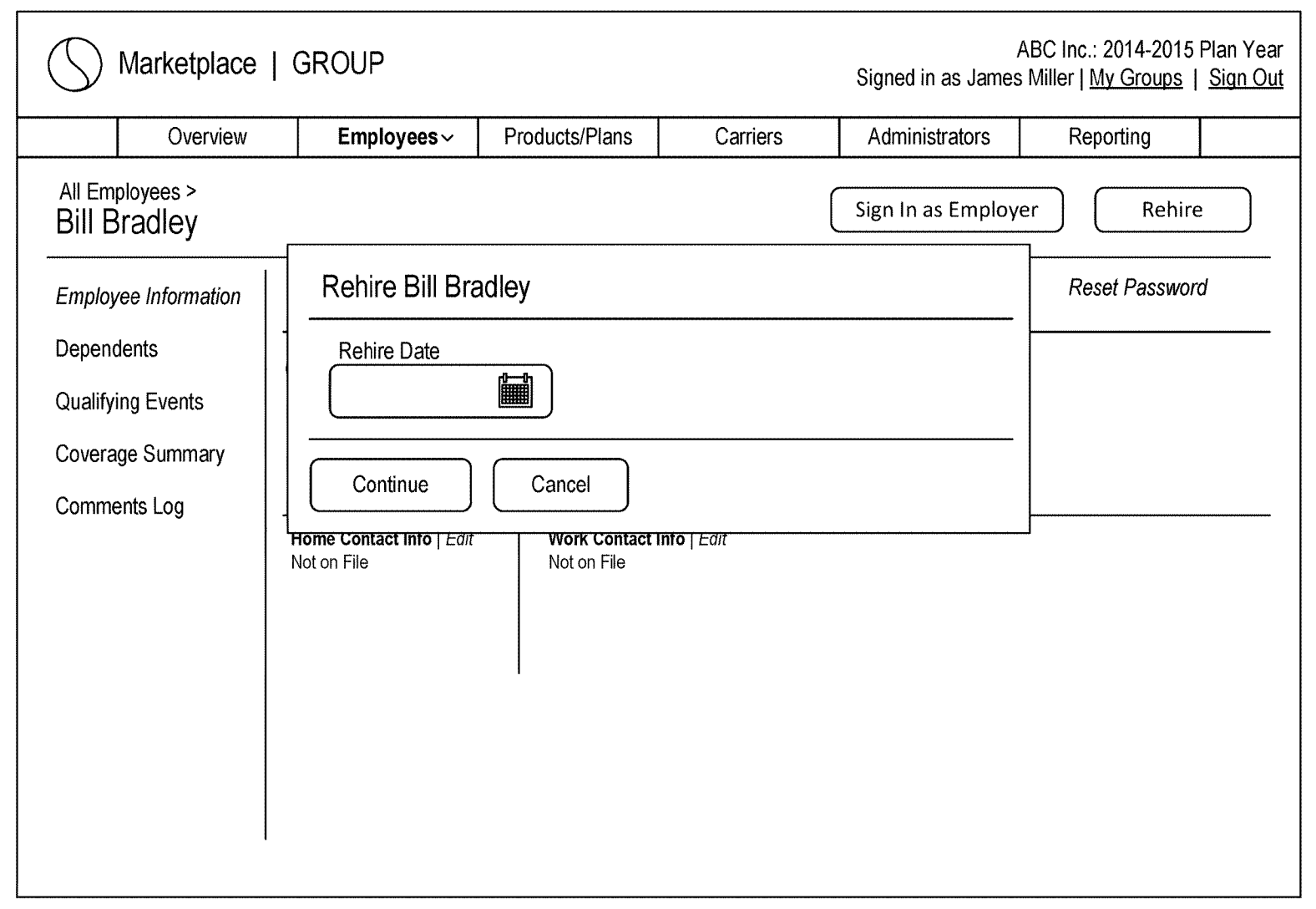

In one or more preferred implementations, an employee information interface allows a user to terminate an employee, e.g. via use of a "Terminate" button, as illustrated in FIG. 26. FIGS. 26-28 illustrate a workflow allowing a group administrator user to specify a termination date, reason for termination, and comments related to the termination, as well as review or specify coverage end dates, for the terminated employee. Once an employee has been terminated, the interface preferably will allow a group administrator user to rehire the employee and specify a rehire date, as illustrated in FIG. 29.

Figure 30:
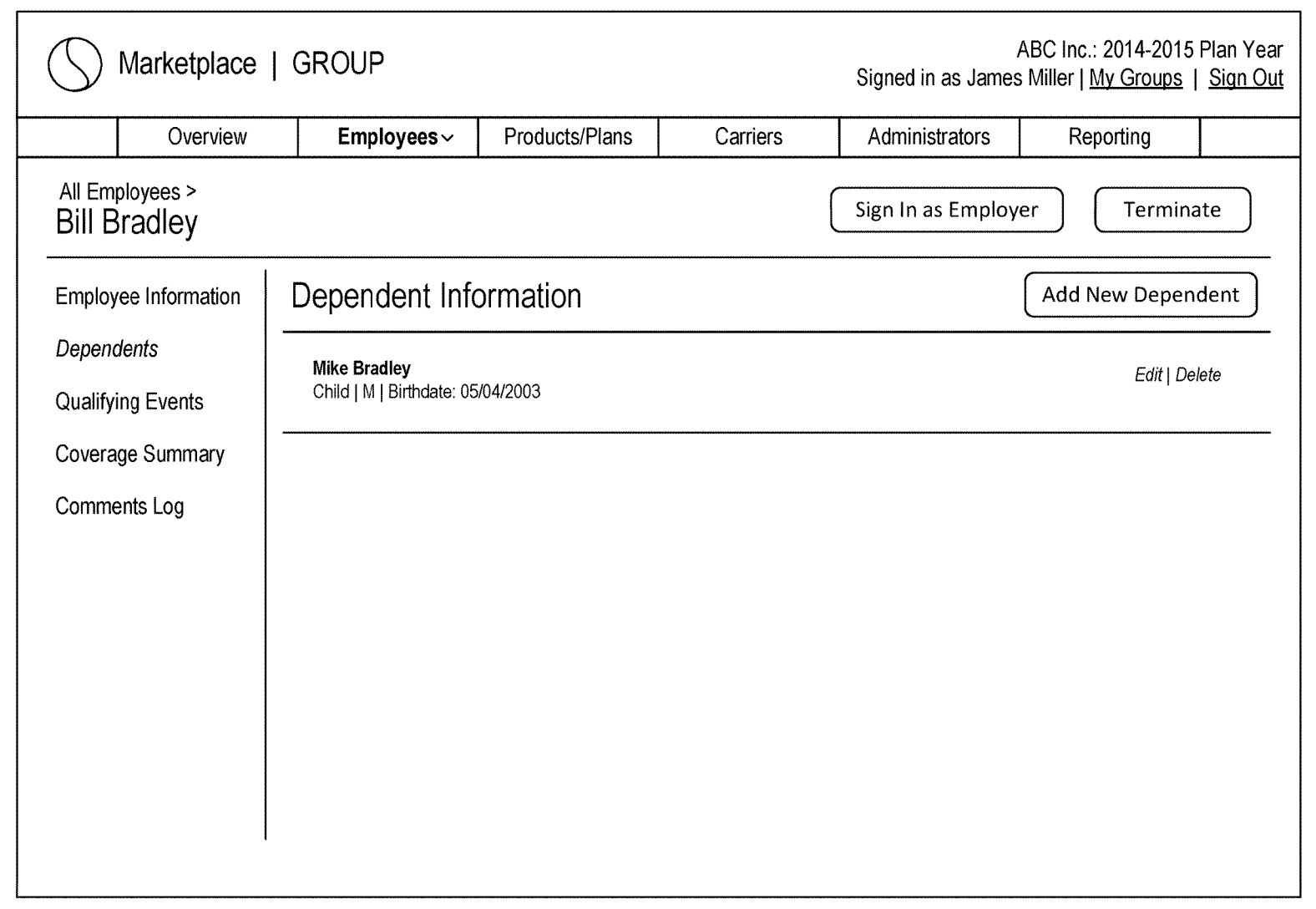
Figure 31A:
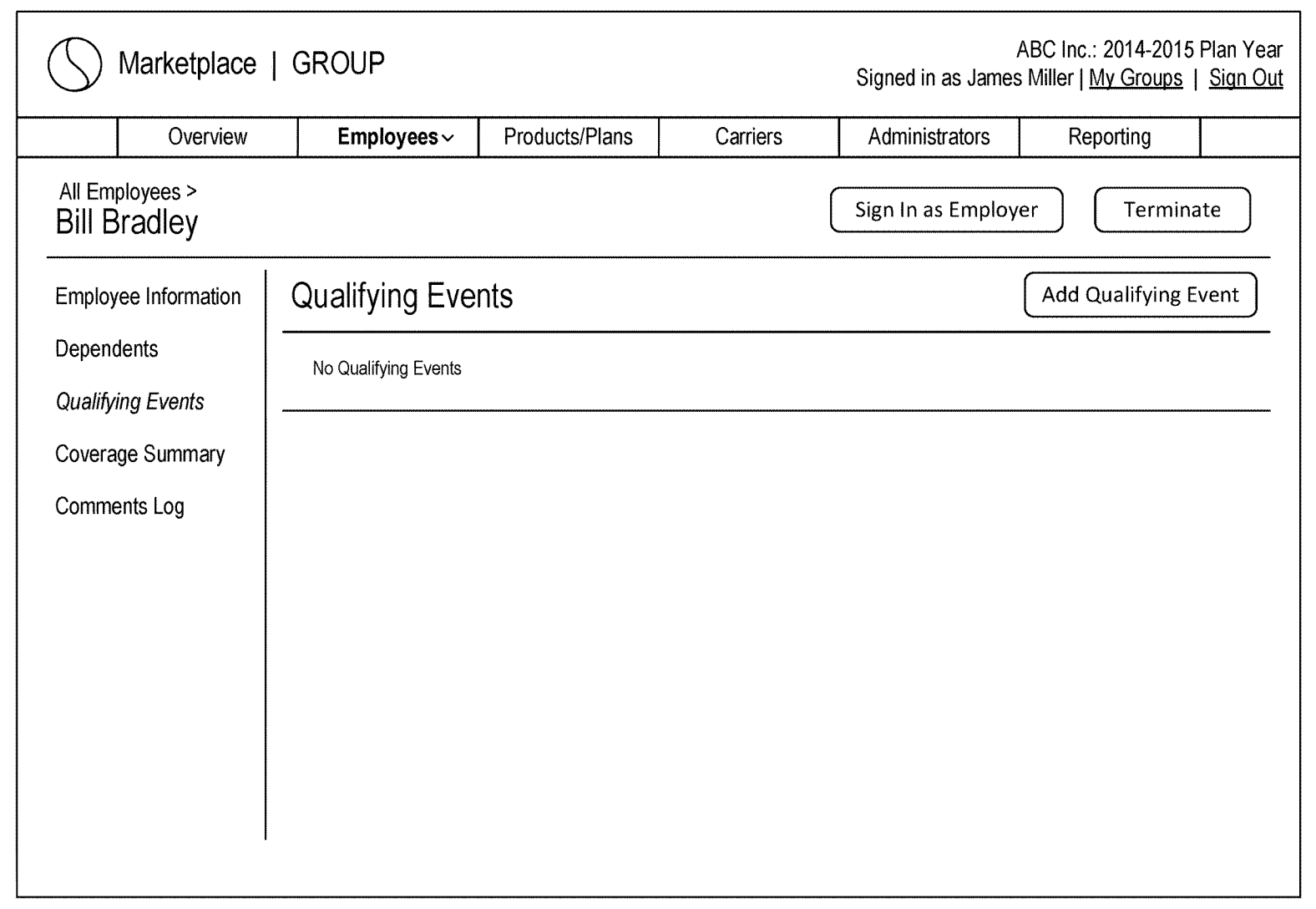
Figure 31B:
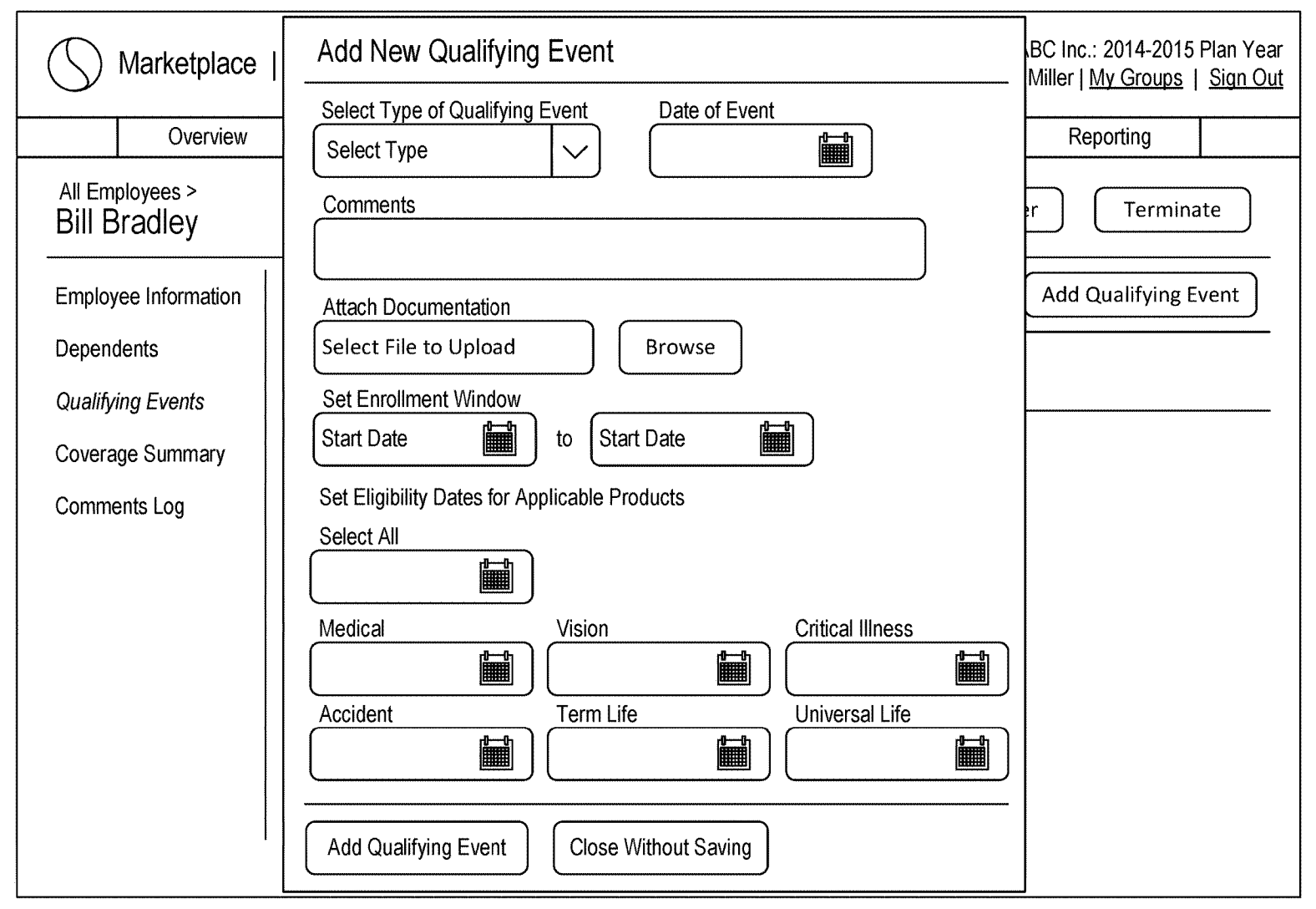

In one or more preferred implementations, a group administrator user can further review and edit dependent information for an employee, as illustrated in FIG. 30, and qualifying events for an employee, as illustrated in FIGS. 31A-B. In one or more preferred implementations, a platform is configured to allow an employee user (described in more detail hereinbelow) to submit a life event enrollment request for review by a group administrator user.

In one or more preferred implementations, a group administrator user can further review a coverage summary for an employee, and even add coverage for an employee, as illustrated in FIG. 32. Preferably, in reviewing coverage information for an employee, a group administrator user can further specify a defined contribution amount for the employee, as illustrated in FIG. 32.

In one or more preferred implementations, in addition to being able to specify a contribution amount for an individual employee via an information interface associated with that employee, a platform provides an interface which allows a group administrator user to review and edit contribution amounts for all employees for the group, as illustrated in FIG. 33. Preferably, an interface allows a group administrator user to specify a total defined contribution amount for each or any employee. Additionally, in one or more preferred implementations, an interface allows a group administrator user to apply a contribution amount globally to all employees in a group, either by specifying an additional contribution amount to globally add to a minimum contribution amount for each employee, or by specifying a total contribution amount to globally apply to each employee, as illustrated in FIG. 33. Thereafter, a group administrator user can edit individual contribution amounts as needed.

In one or more preferred implementations, a group administrator user can further review product/plan information for a group, as illustrated in FIG. 34. Preferably, an interface allows a group administrator user to access additional information, e.g. in the form of a video or brochure, for each product or plan, as illustrated in FIG. 34.

Figure 35:
FIG. 35 illustrates an interface which allows a group administrator user to review carrier information for a group.

In one or more preferred implementations, a group administrator user can further review carrier information for a group, as illustrated in FIG. 35. Preferably, an interface allows a group administrator user to review forms associated with each carrier, and review payment information for each carrier, as illustrated in FIG. 35.

In one or more preferred implementations, a group administrator user can further review and edit administrator information for a group. Preferably, a group administrator user can edit information for an existing group administrator, add a group administrator, or remove a group administrator, as illustrated in FIG. 36.

In one or more preferred implementations, a platform provides reporting functionality to a group administrator. FIG. 37 illustrates an exemplary reporting interface which allows a group administrator user to access a payroll report, demographic report, and enrollment report.

Once a broker user has set up a plan year and a group administrator user has approved the plan year, employee users can select insurance coverage via the platform.

In order to do so, an employee will need to register with the platform to become an employee user, and then log in to the platform, e.g. via a web portal. Preferably, in order to register with the employee web portal, a user needs to verify his or her identity via text, email, or social security number. Preferably, verification via text or email involves communication of a text or email to the employee together with a verification link or code, while verification via social security number involves entry by the employee of his or her social security number.

In one or more preferred implementations, following verification, an employee can complete his or her registration by setting a password, setting one or more security questions, and providing additional personal information and dependent information.

In one or more preferred implementations, a platform is configured to facilitate a determination as to whether the employee qualifies for a federal subsidy on a public health exchange. In one or more preferred implementations, this may occur as part of an employee registration process, or upon initially logging in to the platform.

In one or more preferred implementations, a platform is configured to present plan options to an employee user, and allow an employee user to elect one or more plans for coverage.

Figure 38:
FIG. 38 illustrates an exemplary interface which provides an overview of plan types available for election by an employee user.
Figure 39:
FIG. 39 illustrates an interface which allows an employee user to view available plans.

FIG. 38 illustrates an exemplary interface which provides an overview of plan types available for election by an employee user. This interface allows an employee user to view plans available from his employer for the plan year, as illustrated in FIG. 39. These plans are the plans that were selected by the broker and approved by the group administrator.

As an employee user makes elections for each plan type, a total cost of his elections is preferably displayed, as illustrated in FIG. 40. In one or more preferred implementations, a cost summary may further display an employer contribution amount, and an estimated amount the employee will have to pay, as illustrated in FIG. 41.

In one or more preferred implementations, an interface informs an employee user of a lump sum contribution amount an employer has provided for health insurance, and/or a specific contribution amount an employer will provide for one or more products or coverage tiers. In one or more preferred implementations, specific contribution amounts for specific products or coverage tiers are presented as coupons that can be applied to those specific products or coverage tiers, while lump sum amounts are presented as a bank of funds that can be applied in any manner an employee user desires.

For example, FIG. 42 illustrates exemplary specific employer contribution, or coupon, amounts for various product and coverage combinations. In one or more preferred implementations, these amounts may be presented to an employee as coupons, as illustrated in FIG. 43.

FIG. 44 illustrates an exemplary interface which provides plan information to an employee user for selection of a plan. As illustrated, the interface displays a total plan cost for each plan after an applicable employer coupon.

Figure 45:
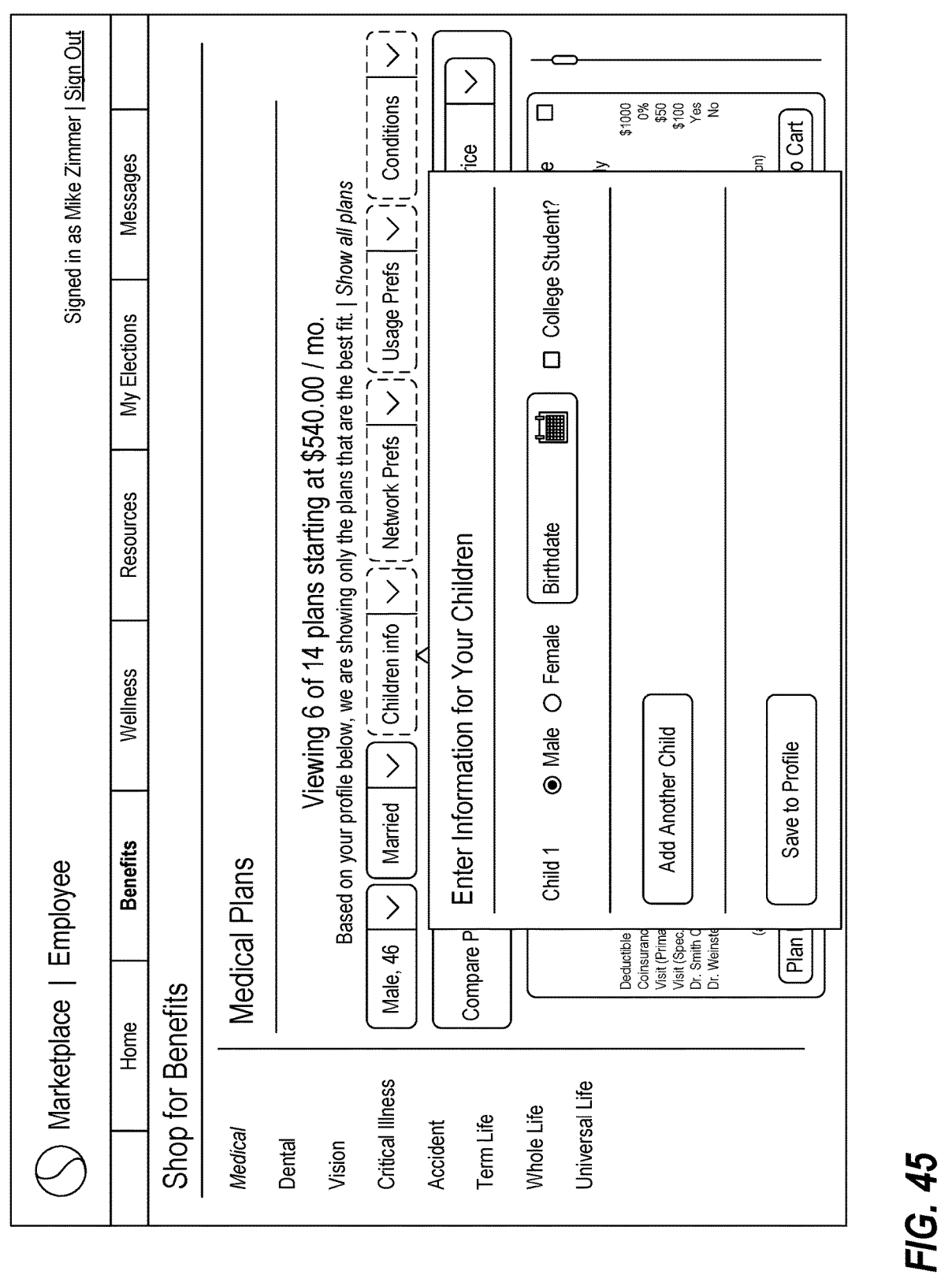

In one or more preferred implementations, a platform includes an editable profile for an employee user which allows an employee user to fill out as much or as little as they like of the profile. Preferably, this profile can be utilized in searching for plans appropriate for the employee user. FIG. 44 illustrates the use of profile information to filter displayed plans. In the illustrated interface, plans are filtered based on the fact that the employee user is male, forty four years old, and married. The employee user can provide additional information to further filter displayed plans. For example, an employee may choose to provide additional information regarding their children, as illustrated in FIG. 45, or may choose not to add such information to their editable profile in shopping for a plan.

Preferably, the platform allows an employee user to compare plans, as illustrated in FIG. 46.

In one or more preferred implementations, an employee user can add plans to a shopping cart such as in a traditional online shopping experience. In one or more preferred implementations, plans in a shopping cart may then be compared to one another.

In one or more preferred implementations, as an employee user adds plans to his or her shopping cart, a cost estimate is updated to indicate the total cost of the selected plans, as illustrated in FIG. 47. In one or more preferred implementations, this cost estimate details both specific contribution amounts (in the form of coupons) an employer will provide for one or more products, as well as a lump sum contribution amount (in the form of a benefit bank) an employer will provide.

Preferably, when an employee is ready to check out, he or she can view his or her shopping cart and estimates for each item therein together with estimates for employer contributions for such items, as illustrated in FIG. 48.

In one or more preferred implementations, if there are any products which require active enrollment, these products are preloaded into the employee's cart and the employee will be required to make a decision as to whether to enroll or decline enrollment.

In one or more preferred implementations, rather than requiring an employee to enroll in each of a plurality of plans one at a time, an employee can utilize a check out button to experience a consolidated check out process flow where all of the inputs for any product are presented in a clear, step-by-step format, as illustrated in FIG. 49. Preferably, any inputs that require explanation are supplemented with in-line help content.

In one or more preferred implementations, upon completing the enrollment process, an easy to read summary of the benefits enrolled in is presented. Preferably, this includes a list of plans along with basic information for each plan and cost information, as well as contact information for an employee's group and broker information for the plan year.

In one or more preferred implementations, a platform provides predefined product bundles. These bundles may be automatically generated utilizing a rules engine, or may be specified by a broker user or a group administrator user. In one or more preferred implementations, these bundles may be refined by an employee user. FIG. 50 illustrates exemplary product bundles. In one or more preferred implementations, such product bundles may be presented in combination with coupons, as illustrated in FIG. 50.

In one or more preferred implementations, if an employee user expresses interest in a plan (e.g. by adding it to his or her shopping cart) and that plan is part of a bundle, the employee user may be alerted to this. Preferably, the employee user is given bundle details, and the option to add the plan by itself, or the bundle, to his or her shopping cart.

Figure 51:
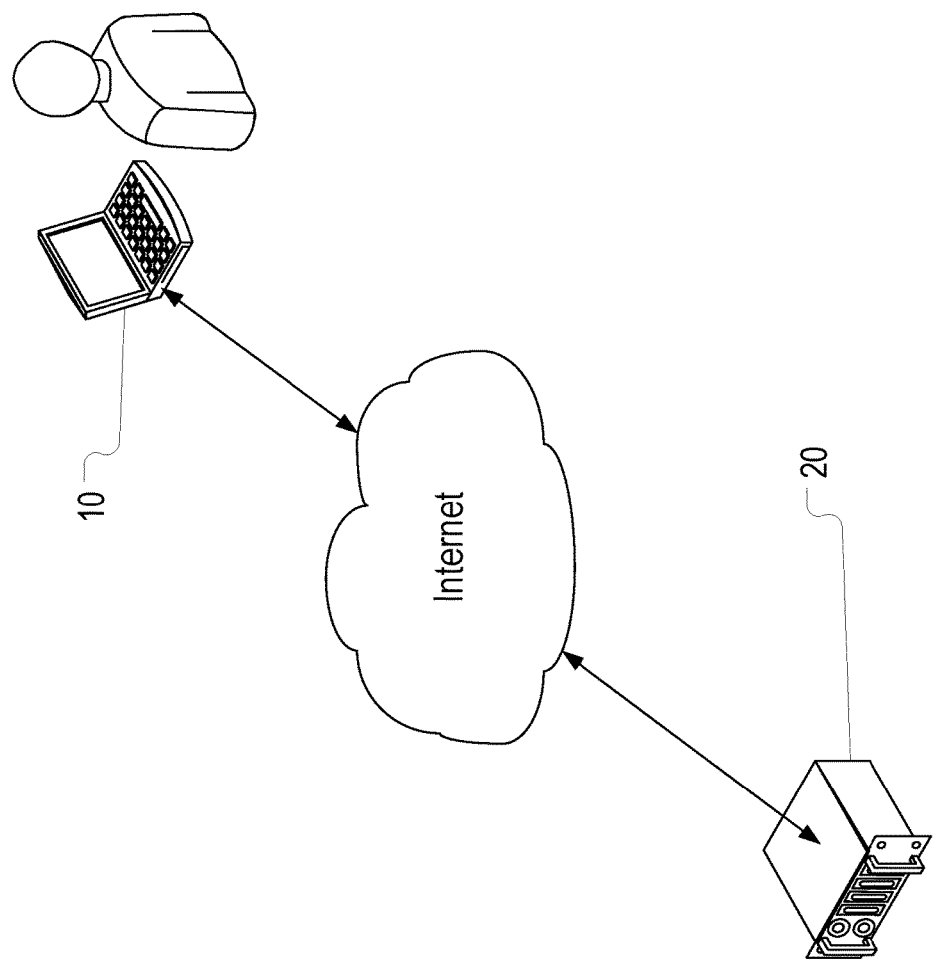
FIG. 51 illustrates an example architecture for an exemplary implementation in which a user accesses a web portal of a platform via a laptop or other computing device.
Figure 52:
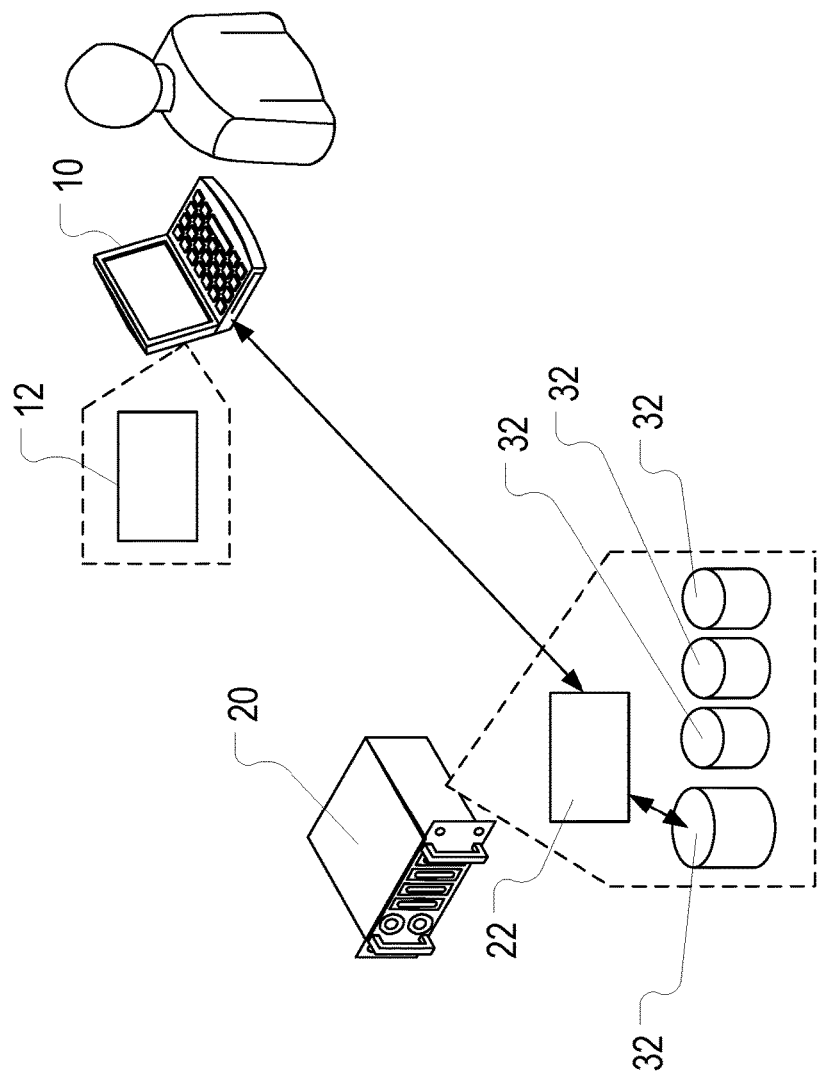
FIG. 52 illustrates a web portal which comprises a web service hosted at one or more web servers.
Figure 53:
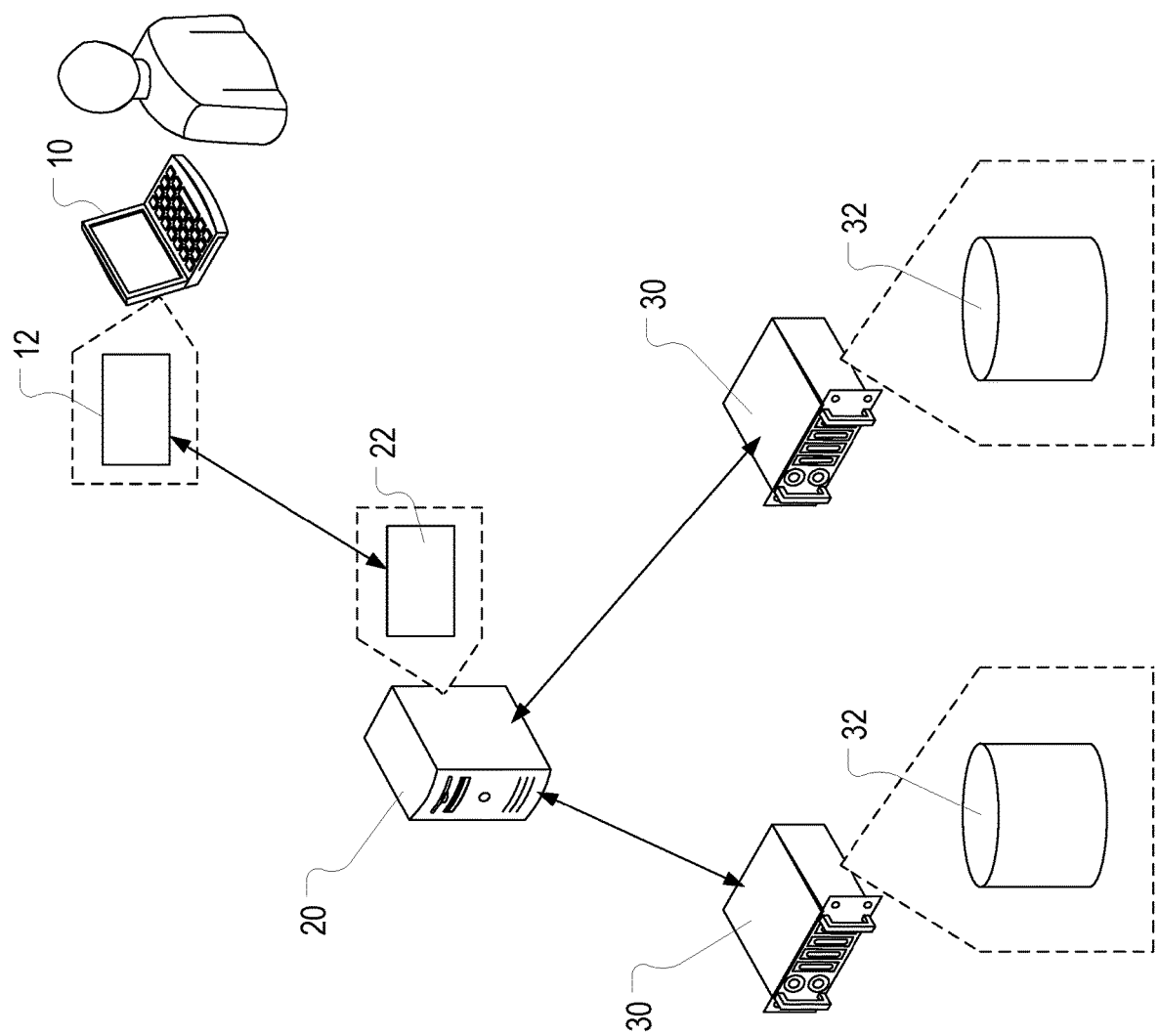
FIG. 53 illustrates a web portal which comprises a web service hosted at one or more remote machines such as a database server.

Various implementations utilizing a platform are disclosed herein. It will be appreciated that disclosed platforms may be accessible over a network connection, e.g. over the Internet. Such platforms may comprise one or more servers or cloud servers. FIG. 51 illustrates an example architecture for an exemplary implementation in which a user accesses a web portal of a platform via a laptop 10 or other computing device. The web portal comprises a web service 22 hosted at one or more web servers 20, as illustrated in FIG. 52. A web browser application 12 running at a user device 10 may access the web portal by accessing a particular URL or URI which effects communication with the web service 22, as illustrated in FIG. 52. The web portal may be configured to provide access to data from one or more databases 32. These databases may be local to a web server on which the web service 22 is running as illustrated in FIG. 52, or may be remote on another machine such as a database server 30, as illustrated in FIG. 53. In accordance with one or more preferred implementations, one or more web servers and/or database servers may be virtual machines.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof

What is claimed is:

1. A method for allowing a broker to split commissions with one or more co-brokers, the method comprising:
   (a) maintaining, at a broker portal platform, a list of brokers, each broker being associated with one or more insurance products;
   (b) displaying, to a first one of the brokers via an electronic display associated with an electronic device, a broker portal interface for the broker portal platform which includes a search interface configured to allow the first broker to search for other brokers of the list of brokers;
   (c) receiving, from the first broker via one or more input devices associated with the electronic device, input corresponding to indication of one or more search parameters;
   (d) displaying, to the first broker via the electronic display, a broker portal interface for the broker portal platform including brokers of the maintained list of brokers which match the input search parameters;
   (e) receiving, from the first broker via one or more input devices associated with the electronic device, input corresponding to selection of one or more brokers of the displayed brokers which match the input search parameters;
   (f) communicating, to each of the selected brokers, an invitation to join as a co-broker for a particular client;
   (g) receiving, from a second broker of the selected brokers, an indication of acceptance of the invitation;
   (h) associating, at the broker portal platform, the second broker with the particular client;
   (i) displaying, to the first one of the brokers via the electronic display associated with the electronic device, a broker portal interface for the broker portal platform which includes a list of brokers associated with the particular client, including the first broker and the second broker; and
   (j) receiving, from the first broker via one or more input devices associated with the electronic device, input corresponding to a commission share for the second broker for the particular client.

2. The method of claim 1, wherein the electronic display comprises a monitor.

3. The method of claim 1, wherein the electronic display comprises a touchscreen.

4. The method of claim 1, wherein the electronic device comprises a computer.

5. The method of claim 1, wherein the electronic device comprises a tablet.

6. The method of claim 1, wherein the electronic device comprises a phone.

7. The method of claim 1, wherein the first broker is appointed to work with a first group of carriers, and the second broker is appointed to work with a second group of carriers.

8. The method of claim 1, wherein the input one or more search parameters comprise a location.

9. The method of claim 1, wherein the input one or more search parameters comprise a carrier association.

10. The method of claim 1, wherein the input one or more search parameters comprise a name.

11. The method of claim 1, wherein the input one or more search parameters comprise a carrier association and a location.

12. A method for allowing a broker to split commissions with one or more co-brokers, the method comprising:
   (a) maintaining, at a broker portal platform, a list of brokers, each broker being associated with one or more insurance products;
   (b) displaying, to a first one of the brokers via an electronic display associated with an electronic device, a broker portal interface for the broker portal platform which includes a search interface configured to allow the first broker to search for other brokers of the list of brokers;
   (c) receiving, from the first broker via one or more input devices associated with an electronic device, input corresponding to indication of one or more search parameters;
   (d) displaying, to the first broker via an electronic display associated with an electronic device, a broker portal interface for the broker portal platform including brokers of the maintained list of brokers which match the input search parameters;
   (e) receiving, from the first broker via one or more input devices associated with an electronic device, input corresponding to selection of one or more brokers of the displayed brokers which match the input search parameters;
   (f) communicating, to each of the selected brokers, an invitation to join as a co-broker for a particular client;
   (g) receiving, from a second broker of the selected brokers, an indication of acceptance of the invitation;
   (h) associating, at the broker portal platform, the second broker with the particular client;
   (i) displaying, to the first one of the brokers via an electronic display associated with an electronic device, a broker portal interface for the broker portal platform which includes a list of brokers associated with the particular client, including the first broker and the second broker; and
   (j) receiving, from the first broker via one or more input devices associated with an electronic device, input corresponding to a commission share for the second broker for the particular client.

13. The method of claim 12, wherein the first broker is appointed to work with a first group of carriers, and the second broker is appointed to work with a second group of carriers.

14. The method of claim 12, wherein the input one or more search parameters comprise a location.

15. The method of claim 12, wherein the input one or more search parameters comprise a carrier association.

16. The method of claim 12, wherein the input one or more search parameters comprise a name.

17. One or more non-transitory computer readable media containing computer executable instructions for performing a method for allowing a broker to split commissions with one or more co-brokers, the method comprising:
   (a) maintaining, at a broker portal platform, a list of brokers, each broker being associated with one or more insurance products;
   (b) displaying, to a first one of the brokers via an electronic display associated with an electronic device, a broker portal interface for the broker portal platform which includes a search interface configured to allow the first broker to search for other brokers of the list of brokers;

(c) receiving, from the first broker via one or more input devices associated with the electronic device, input corresponding to indication of one or more search parameters;
(d) displaying, to the first broker via the electronic display, a broker portal interface for the broker portal platform including brokers of the maintained list of brokers which match the input search parameters;
(e) receiving, from the first broker via one or more input devices associated with the electronic device, input corresponding to selection of one or more brokers of the displayed brokers which match the input search parameters;
(f) communicating, to each of the selected brokers, an invitation to join as a co-broker for a particular client;
(g) receiving, from a second broker of the selected brokers, an indication of acceptance of the invitation;
(h) associating, at the broker portal platform, the second broker with the particular client;
(i) displaying, to the first one of the brokers via the electronic display associated with the electronic device, a broker portal interface for the broker portal platform which includes a list of brokers associated with the particular client, including the first broker and the second broker; and
(j) receiving, from the first broker via one or more input devices associated with the electronic device, input corresponding to a commission share for the second broker for the particular client.

18. The method of claim 1, wherein the method further includes a process for facilitating employee selection of one or more health insurance products comprising:
(a) maintaining, at an insurance portal platform, employer contribution information including
  (i) a plurality of specific defined contribution amounts for each of a plurality of classes of health insurance products, including, for each class of product,
    (A) an amount for enrollment of an employee,
    (B) an amount for enrollment of an employee and his or her spouse,
    (C) an amount for enrollment of an employee and his or her children, and
    (D) an amount for enrollment of an employee and his family; and
  (ii) a lump sum defined contribution amount;
(b) displaying, to a user via an electronic display associated with an electronic device, a login interface for the insurance portal platform;
(c) receiving, from the user via one or more input devices associated with the electronic device, input corresponding to login credentials for the user;
(d) determining, by the insurance portal platform, that the user is an employee of the employer, and, based thereon, displaying, to the user via the electronic display, a plurality of specific defined contribution amounts for each of a plurality of classes of health insurance products, including, for each class of product,
  (i) an amount for enrollment of an employee,
  (ii) an amount for enrollment of an employee and his or her spouse,
  (iii) an amount for enrollment of an employee and his or her children, and
  (iv) an amount for enrollment of an employee and his family; and
(e) displaying, to the user via the electronic display, information regarding a plurality of insurance products including, for each product,
  (i) a coupon amount the cost of that product will be discounted based on a specific defined contribution amount for that class of health insurance product, and
  (ii) an estimated monthly cost after the coupon amount is applied;
(f) receiving, from the user via one or more input devices associated with the electronic device, input corresponding to selection of a health insurance product;
(g) displaying, to the user via the electronic display, information regarding the selected insurance product including
  (i) an estimated cost of a plan including the selected health insurance product,
  (ii) a coupon amount the cost of the plan will be discounted based on a specific defined contribution amount for the class of the selected health insurance product, and
  (iii) a lump sum defined contribution amount the cost of the plan will be discounted, and
  (iv) an estimated monthly cost after the coupon amount and lump sum defined contribution amount are applied.

19. The method of claim 1, wherein the method further includes a process for facilitating employee selection of one or more health insurance products comprising:
(a) maintaining, at an insurance portal platform, information regarding a plurality of health insurance products available for employees of an employer;
(b) displaying, to a user via an electronic display associated with an electronic device, a login interface for the insurance portal platform;
(c) receiving, from the user via one or more input devices associated with the electronic device, input corresponding to login credentials for the user;
(d) determining, by the insurance portal platform, that the user is an employee of the employer, and, based thereon, determining one or more health insurance products which require an active enrollment decision by the user;
(e) preloading, into a user shopping cart of the insurance portal platform for the user, the one or more health insurance products determined to require an active enrollment decision by the user;
(f) receiving, from the user via one or more input devices associated with the electronic device, input corresponding to accessing the shopping cart; and
(g) displaying, to the user via the electronic display, the shopping cart which includes the one or more health insurance products determined to require an active enrollment decision by the user.

20. The method of claim 1, wherein the method further includes a process for allowing a broker to selectively hide commission information for presentation of insurance plan information to a client, the process comprising:
(a) displaying, to a broker on an electronic display associated with an electronic device, a broker portal interface in a broker display mode including
  (i) health insurance plan information for a client of the broker,
  (ii) broker commission information for the broker, and
  (iii) a toggle interface element configured to allow the broker to toggle to a face-to-face display mode; and (b) receiving, from the broker via one or more input devices associated with the electronic device, input corresponding to engagement of the toggle interface element; and
(c) displaying, on the electronic display in response to the input corresponding to engagement of the toggle interface element, a broker portal interface in the face-to-face display mode including
  (i) health insurance plan information for a client of the broker, and
  (ii) a toggle interface element configured to allow the broker to toggle to the broker display mode,
  (iii) wherein the broker portal interface in the face-to-face display mode does not include broker commission information.

* * * * *